US011419946B2

(12) United States Patent
Tsubusaki et al.

(10) Patent No.: US 11,419,946 B2
(45) Date of Patent: Aug. 23, 2022

(54) HETEROBIFUNCTIONAL MONODISPERSED POLYETHYLENE GLYCOL AND CONJUGATE USING SAME

(71) Applicant: NOF CORPORATION, Tokyo (JP)

(72) Inventors: Takuma Tsubusaki, Kawasaki (JP); Kohei Yoshimura, Kawasaki (JP); Mika Hamura, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 16/493,431

(22) PCT Filed: Mar. 23, 2018

(86) PCT No.: PCT/JP2018/011883
§ 371 (c)(1),
(2) Date: Sep. 12, 2019

(87) PCT Pub. No.: WO2018/181059
PCT Pub. Date: Oct. 4, 2018

(65) Prior Publication Data
US 2020/0000933 A1  Jan. 2, 2020

(30) Foreign Application Priority Data
Mar. 30, 2017 (JP) .............................. JP2017-066987

(51) Int. Cl.
*A61K 47/68* (2017.01)
*A61K 47/60* (2017.01)
*A61K 31/704* (2006.01)
*C08G 65/333* (2006.01)
*C08G 65/329* (2006.01)

(52) U.S. Cl.
CPC ........ *A61K 47/6889* (2017.08); *A61K 31/704* (2013.01); *A61K 47/60* (2017.08); *C08G 65/329* (2013.01); *C08G 65/33396* (2013.01)

(58) Field of Classification Search
CPC .. A61K 47/6889; A61K 47/60; A61K 31/704; C08G 65/33396
See application file for complete search history.

(56) References Cited

U.S. PATENT DOCUMENTS

| 2007/0166808 A1 | 7/2007 | Zhao et al. |
| 2011/0245509 A1* | 10/2011 | Nakamoto ....... C08G 65/33337 548/546 |
| 2012/0077988 A1 | 3/2012 | Yamamoto et al. |
| 2012/0282671 A1 | 11/2012 | Zhao et al. |
| 2013/0022669 A1 | 1/2013 | Axelsson et al. |
| 2013/0225789 A1 | 8/2013 | Sun et al. |
| 2018/0312466 A1 | 11/2018 | Yamamoto et al. |

FOREIGN PATENT DOCUMENTS

| CN | 102822235 A | 12/2012 |
| JP | 2009-523898 A | 6/2009 |
| JP | 2011-523628 A | 8/2011 |
| JP | 2011-225860 A | 11/2011 |
| JP | 2012-25932 A | 2/2012 |
| JP | 2013-515791 A | 5/2013 |
| JP | 2013-523943 A | 6/2013 |
| WO | 2007/084808 A2 | 7/2007 |
| WO | 2009/134976 A1 | 11/2009 |
| WO | 2015057699 A2 | 4/2015 |
| WO | 2016/0063006 A1 | 4/2016 |

OTHER PUBLICATIONS

Zacchigna et al. (Polymers 2011, 3, 1076-1090).*
Robert P. Lyon, et al., "Reducing hydrophobicity of homogeneous antibody-drug conjugates improves pharmacokinetics and therapeutic index", Nature Biotechnology, vol. 33, No. 7, 2015, pp. 733-736 (4 pages total).
International Search Report (PCT/ISA/210) dated Jun. 26, 2018 issued by the International Searching Authority in International Application No. PCT/JP2018/011883.
Written Opinion (PCT/ISA/237) dated Jun. 26, 2018 issued by the International Searching Authority in International Application No. PCT/JP2018/011883.
Communication dated Dec. 21, 2020 issued by the European Patent Office in European Application No. 18778251.1.
Muraoka, T., et al., "Supporting Information—A Structured Monodisperse PEG for the Effective Suppression of Protein Aggregation", Angewandte Chemie International Edition, vol. 52, No. 9, 2430-2434, Jan. 30, 2013, pp. s1-s33.
Office Action dated Jul. 5, 2021, by the Japan Patent Office in corresponding Japanese Patent Application No. 2018-055594.
Office Action dated Jul. 13, 2021, by the State Intellectual Property Office of P.R. China in corresponding Chinese Patent Application No. 201880023156.8.
Communication dated Oct. 10, 2021 issued by the Intellectual Property India in application No. 201947038521.
Communication dated Apr. 18, 2022 by the Korean Intellectual Property Office in Korean Patent Application No. 10-2019-7028712.

* cited by examiner

*Primary Examiner* — Robert H Havlin
(74) *Attorney, Agent, or Firm* — Sughrue Mion, PLLC

(57) ABSTRACT

A heterobifunctional monodispersed polyethylene glycol represented by formula (1) which has two adjacent monodispersed polyethylene glycol side chains and does not have a chiral center in the molecular structure:

$$R^1-(OCH_2CH_2)_n-O-CH_2 \diagdown \atop C \diagup A^1-X^1$$
$$R^1-(OCH_2CH_2)_n-O-CH_2 \diagup \quad \diagdown B^1-Y^1 \qquad (1)$$

wherein $X^1$ and $Y^1$ are each an atomic group containing a functional group capable of forming a covalent bond upon a reaction with a functional group present in a biofunctional molecule. $R^1$ is a hydrocarbon group or the like. n is an integer of 3 to 72. $A^1$ represents $-L^1-(CH_2)_{m1}-$ or the like, $L^1$ and $L^2$ represent each an ether bond or the like, and m1 and m2 each independently represent an integer of 1 to 5. $B^1$ represents $-L^3-(CH_2)_{m3}-$ or the like, $L^3$ and $L^4$ represent an amide bond or the like, and m3 and m4 each independently represent an integer of 1 to 5. Also disclosed is an antibody-drug conjugate including the heterobifunctional monodispersed polyethylene glycol.

2 Claims, 5 Drawing Sheets

HETEROBIFUNCTIONAL MONODISPERSED POLYETHYLENE GLYCOL AND CONJUGATE USING SAME

CROSS REFERENCE TO RELATED APPLICATIONS

This application is a National Stage of International Application No. PCT/JP2018/011883 filed Mar. 23, 2017, claiming priority based on Japanese Patent Application No. 2017-066987 filed Mar. 30, 2017, the above-noted applications incorporated herein by reference in their entirety.

TECHNICAL FIELD

The present invention relates to a heterobifunctional monodispersed polyethylene glycol having two different chemically reactive functional groups. More particularly, it relates to a heterobifunctional monodispersed polyethylene glycol, which is used for modification of a biofunctional molecule, for example, a physiologically active protein, a peptide, an antibody, a nucleic acid or a low molecular weight drug, a drug carrier in a drug delivery system, a diagnostic material, a medical device or the like and which is particularly useful for modification of an antibody drug, and a conjugate using the same.

BACKGROUND ART

An antibody-drug conjugate (Antibody-Drug Conjugate: ADC) is an antibody drug in which a drug is bonded to an antibody and which aims to actively carry the drug to a disease site by utilizing the antigen specificity of the antibody, and in recent years, it is one of the most rapidly growing techniques in the field of cancer treatment. The ADC is composed of each part of an antibody, a drug and a linker for bonding between the antibody and the drug.

Many of the drugs used in ADC are hydrophobic and when a plurality of these hydrophilic drugs are bonded to an antibody to prepare ADC, there is a problem of occurrence of aggregation or decrease in stability of the antibody in blood caused by the hydrophobicity of the drugs. Thus, the number of the drugs which can be mounted per antibody is restricted and as a result, the medical effect of ADC cannot be sufficiently obtained in some cases.

One of the solutions to be investigated for the problem is the use of a hydrophilic linker. As the hydrophilic linker, polyethylene glycol, a hydrophilic peptide, a sugar chain and the like are used. In particular, since polyethylene glycol has low antigenicity and a high biocompatibility, it is used in a plurality of ADC in a clinical trial or preclinical trial stage.

In the field of ADC, for the purpose of guaranteeing the uniformity of ADC and simplifying purification, analysis and drug approval application, a compound containing 90% or more of a component having a specific ethylene glycol chain length is used. Such a compound is referred to as monodispersed polyethylene glycol.

In the case where the monodispersed polyethylene glycol is used as a linker for ADC, since it is necessary to separately bond an antibody and a drug, a heterobifunctional monodispersed polyethylene glycol having two different chemically reactive functional groups is utilized. In general, a compound having the chemically reactive functional groups different from each other at both terminals of a monodispersed polyethylene glycol chain is used to prepare ADC.

However, in recent years, ADC in which a monodispersed polyethylene glycol is not used as a linker main chain inking an antibody and a drug, and a monodispersed polyethylene glycol is introduced as a side chain of a branched linker linking an antibody and a drug is reported.

In Non Patent Literature 1, as to ADC in which a monodispersed polyethylene glycol is used as a linker main chain inking an antibody and a drug and ADC in which a monodispersed polyethylene glycol is used as a side chain of a branched linker linking an antibody and a drug, the pharmacokinetics and therapeutic effect thereof are compared and it is reported that the latter ADC has a high masking effect to the hydrophobicity of the drug and exhibits the excellent pharmacokinetics and therapeutic effect.

Further, in Patent Literature 2 and Patent Literature 3, various types of ADC having a monodispersed polyethylene glycol as a side chain of a branched linker and intermediates for preparing these ADC are disclosed.

In addition, in Patent Literature 1, a polyethylene glycol derivative in which two polyethylene glycol chains and two functional groups are bonded to a pentaerythritol backbone is described.

CITATION LIST

Patent Literature

Patent Literature 1: JP-A-2011-225860
Patent Literature 2: WO2015/057699
Patent Literature 3: WO2016/063006

Non Patent Literature

Non Patent Literature 1: Nature Biotechnology, 2015, 33, 733-735

SUMMARY OF INVENTION

Problem to be Solved by the Invention

In Patent Literature 1, a compound in which two same functional groups and two same polyethylene glycol chains are bonded to a pentaerythritol backbone is only disclosed. This is because in a reaction of functionalization, two hydroxy groups of pentaerythritol are protected with a protective group, after addition of EO the protective group is removed and then the functionalization is performed.

In ADC having a monodispersed polyethylene glycol as a side chain of a branched linker as described in Non Patent Literature 1, Patent Literature 2 or Patent Literature 3, an amino acid having an asymmetric carbon in a branched portion of the linker to which the monodispersed polyethylene glycol is bonded is used.

In the case where a linker of a desired chemical structure is constructed through a various chemical conversion processes using a compound having such a chiral center, a not-desired partial steric inversion or racemization of the chiral center occurs in, for example, acidic or basic reaction conditions, a reaction in the presence of an organic catalyst or inorganic catalyst, or a reaction in the presence of a condensing agent included in the chemical conversion process, and thus there is a possibility to form a mixture of stereoisomers. It is extremely difficult to isolate a compound having a desired three-dimensional structure from the mixture of stereoisomers. It is not preferred to use such a mixture of stereoisomers as a linker for linking an antibody and a drug, because a heterogeneous ADC is formed.

Further, in Patent Literature 2 or Patent Literature 3, ADC having two or more monodispersed polyethylene glycols in the side chain of a branched linker are also disclosed. However, the bonding positions of the respective monodispersed polyethylene glycol side chains are separated and the masking effect to the hydrophobic drug due to the umbrella-like structure (Biomaterials 2001, 22(5), 405-417), which is the feature of branched polyethylene glycol having a plurality of polyethylene glycol chains, is small so that the advantage due to the presence of a plurality of monodispersed polyethylene glycol side chains cannot be effectively utilized.

An object of the invention is to provide a heterobifunctional monodispersed polyethylene glycol which has two adjacent monodispersed polyethylene glycol side chains and does not have a chiral center in the molecular structure, and an antibody-drug conjugate in which an antibody and a drug are bonded by using the same.

Means for Solving the Problem

As a result of the intensive investigations to solve the problem described above, the inventors have developed a heterobifunctional monodispersed polyethylene glycol in which two monodispersed polyethylene glycol side chains are closely bonded to each other and which does not have a chiral center in the molecular structure, and an antibody-drug conjugate in which an antibody and a drug are bonded by using the same.

Further, since in the heterobifunctional monodispersed polyethylene glycol of the invention two monodispersed polyethylene glycol chains are bonded to a quaternary carbon atom of the branched portion by a stable ether bond, it has the feature that it is difficult to be decomposed into a single-chain monodispersed polyethylene glycol in the chemical conversion process of the structure of the heterobifunctional monodispersed polyethylene glycol.

Thus, the present invention is as follows.

[1] A heterobifunctional monodispersed polyethylene glycol represented by formula (1):

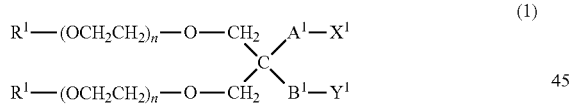

(1)

(in formula (1), $X^1$ and $Y^1$ are each an atomic group containing at least a functional group capable of forming a covalent bond upon a reaction with a functional group present in a biofunctional molecule, the functional group contained in the atomic group $X^1$ and the functional group contained in the atomic group $Y^1$ are different from each other; $R^1$ is a hydrocarbon group having from 1 to 7 carbon atoms or a hydrogen atom; n is an integer of 3 to 72; $A^1$ represents $-L^1-(CH_2)_{m1}-$, $-L^1-(CH_2)_{m1}-L^2-(CH_2)_{m2}-$ or a single bond, $L^1$ represents an ether bond, an amide bond, an urethane bond, a secondary amino group or a single bond, $L^2$ represents an ether bond, an amide bond or an urethane bond, and m1 and m2 represent each independently an integer of 1 to 5; and $B^1$ represents $-L^3-(CH_2)_{m3}-$, $-L^3-(CH_2)_{m3}-L^4-(CH_2)_{m4}-$ or a single bond, $L^3$ represents an amide bond or a single bond, $L^4$ represents an ether bond, an amide bond or an urethane bond, and m3 and m4 represent each independently an integer of 1 to 5.)

[2] The heterobifunctional monodispersed polyethylene glycol of [1], wherein, in formula (1), $A^1$ is represented by $-NHC(O)-(CH_2)_{m1}-$ or $-NHC(O)-(CH_2)_{m1}-L^2-(CH_2)_{m2}-$, and $B^1$ is represented by $-(CH_2)_{m3}-$ or $-(CH_2)_{m3}-L^4-(CH_2)_{m4}-$.

[3] The heterobifunctional monodispersed polyethylene glycol of [1], wherein, in formula (1), $A^1$ is represented by $-CH_2-$ or $-CH_2-L^2-(CH_2)_{m2}-$, and $B^1$ is represented by $-CH_2-$ or $-CH_2-L^4-(CH_2)_{m4}-$.

[4] The heterobifunctional monodispersed polyethylene glycol of [1], wherein, in formula (1), $A^1$ is represented by $-O-(CH_2)_{m1}-$ or $-O-(CH_2)_{m1}-L^2-(CH_2)_{m2}-$, and $B^1$ is represented by $-CH_2-$ or $-CH_2-L^4-(CH_2)_{m4}-$.

[5] The heterobifunctional monodispersed polyethylene glycol of [1], wherein, in formula (1), $A^1$ is represented by $-C(O)NH-(CH_2)_{m1}-$ or $-C(O)NH-(CH_2)_{m1}-L^2-(CH_2)_{m2}-$, and $B^1$ is represented by $-CH_2-$ or $-CH_2-L^4-(CH_2)_{m4}-$.

[6] The heterobifunctional monodispersed polyethylene glycol of [1], wherein, in formula (1), $A^1$ is represented by $-C(O)NH-(CH_2)_{m1}-$ or $-C(O)NH-(CH_2)_{m1}-L^2-(CH_2)_{m2}-$, and $B^1$ is represented by $-C(O)NH-(CH_2)_{m3}-$ or $-C(O)NH-(CH_2)_{m3}-L^4-(CH_2)_{m4}-$.

[7] The heterobifunctional monodispersed polyethylene glycol of any one of [1] to [6], wherein $X^1$ and $Y^1$ in formula (l) are each selected from the group consisting of formula (a), formula (b1), formula (b2), formula (c), formula (d), formula (e), formula (f), formula (g), formula (h), formula (i), formula (j), formula (k), formula (l), formula (m), formula (n) and formula (o):

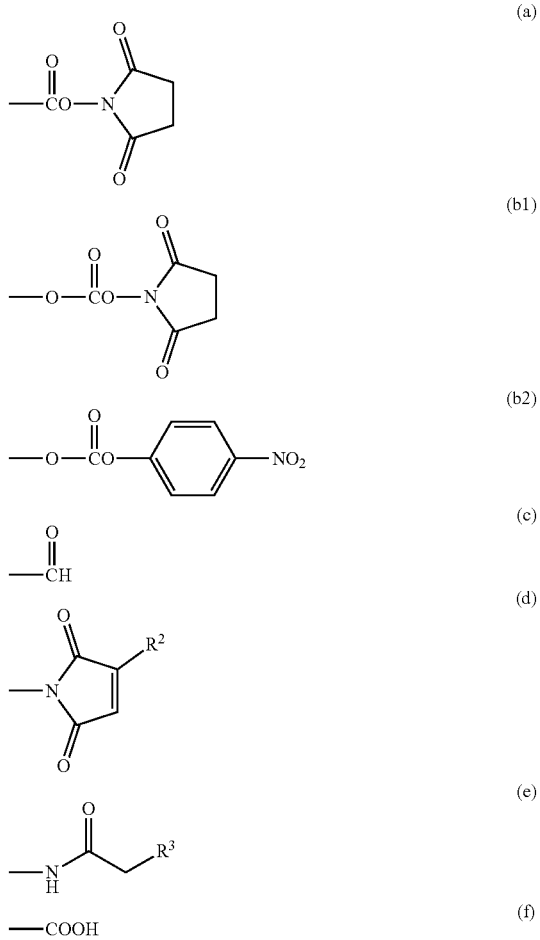

-continued

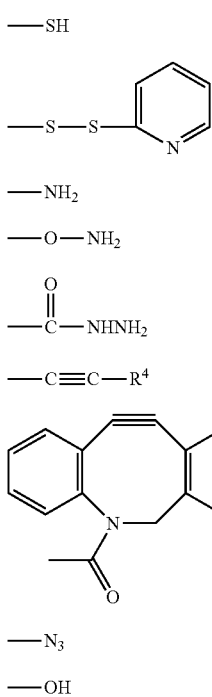

(g) —SH (h) [pyridyl disulfide structure]

(i) —NH₂

(j) —O—NH₂

(k) —C(=O)—NHNH₂

(l) —C≡C—R⁴

(m) [dibenzocyclooctyne structure]

(n) —N₃

(o) —OH (in formula (d), $R^2$ is a hydrogen atom or a hydrocarbon group having from 1 to 5 carbon atoms; in formula (e), $R^3$ is a halogen atom selected from a chlorine atom, a bromine atom and an iodine atom; and in formula (1), $R^4$ is a hydrogen atom or a hydrocarbon group having from 1 to 5 carbon atoms.

[8] An antibody-drug conjugate containing a heterobifunctional monodispersed polyethylene glycol represented by formula (2):

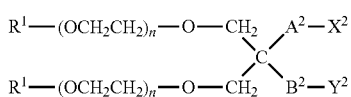

(2)

(in formula (2), one of $X^2$ and $Y^2$ is an antibody, and the other is a drug; $R^1$ is a hydrocarbon group having from 1 to 7 carbon atoms or a hydrogen atom; n is an integer of 3 to 72; $A^2$ represents -$L^1$-$(CH_2)_{m1}$-$L^5$-, -$L^1$-$(CH_2)_{m1}$-$L^2$-$(CH_2)_{m2}$-$L^5$- or a single bond, $L^1$ represents an ether bond, an amide bond, an urethane bond, a secondary amino group or a single bond, $L^2$ represents an ether bond, an amide bond or an urethane bond, m1 and m2 represent each independently an integer of 1 to 5, and $L^5$ is an amide bond, an urethane bond, a thioether bond, a disulfide bond, a carbonate bond, an ester bond, an ether bond, a 1H-1,2,3-triazole-1,4-diyl structure, a secondary amino group, a hydrazide group, an oxyamide group or a hydrocarbon group containing any of them; and $B^2$ represents -$L^3$-$(CH_2)_{m3}$-$L^6$-, -$L^3$-$(CH_2)_{m3}$-$L^4$-$(CH_2)_{m4}$-$L^6$- or a single bond, $L^3$ represents an amide bond or a single bond, $L^4$ represents an ether bond, an amide bond or an urethane bond, m3 and m4 represent each independently an integer of 1 to 5, and $L^6$ is an amide bond, an urethane bond, a thioether bond, a disulfide bond, a carbonate bond, an ester bond, an ether bond, a 1H-1,2,3-triazole-1,4-diyl structure, a secondary amino group, a hydrazide group, an oxyamide group or a hydrocarbon group containing any of them.

Effect of the Invention

Since the heterobifunctional monodispersed polyethylene glycol of the invention does not have a chiral center, a problem of the not-desired partial steric inversion or racemization of the chiral center does not fundamentally occur in the chemical conversion process and since two monodispersed polyethylene glycol chains are bonded to a quaternary carbon atom of the branched portion by a stable ether bond, it is difficult to be decomposed into a single-chain monodispersed polyethylene glycol in the chemical conversion process. Therefore, an antibody-drug conjugate having high homogeneity can be obtained by bonding an antibody and a drug using the heterobifunctional monodispersed polyethylene glycol.

Further, since in the heterobifunctional monodispersed polyethylene glycol two monodispersed polyethylene glycol side chains are closely bonded to each other, when an antibody-drug conjugate is prepared, the masking effect to the hydrophobic drug is large so that the occurrence of aggregation or decrease in stability of the antibody in blood caused by the hydrophobicity of the drug can be suppressed.

EMBODIMENTS FOR CARRYING OUT THE INVENTION

Figure 1:
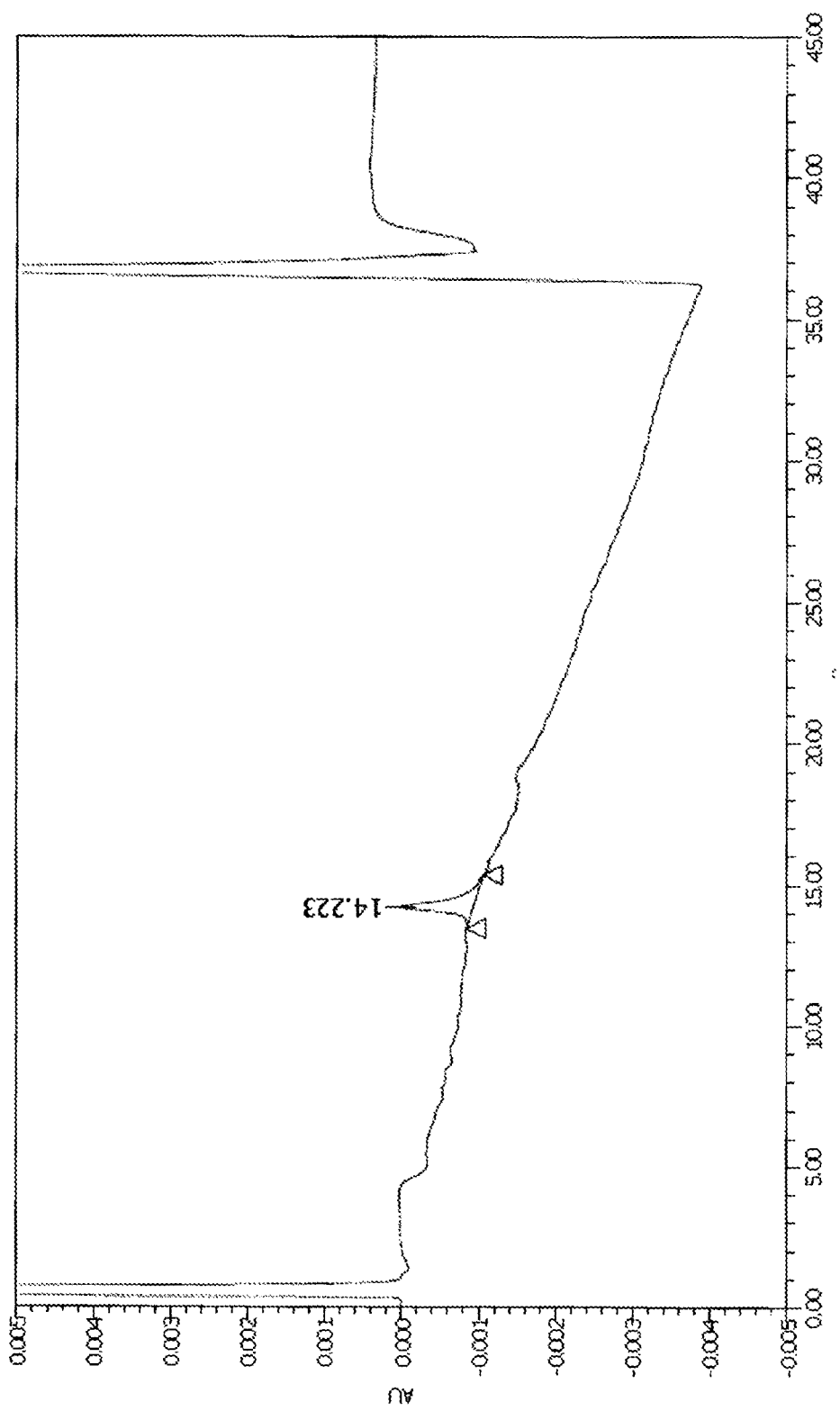
FIG. 1 is a chart of HPLC measurement using a hydrophobic interaction chromatography (HIC) column of Example 8.

The invention will be described in detail below.

In the specification, the term "heterobifunctional" as used means to have two different chemically reactive functional groups, and the term "monodispersed polyethylene glycol" referrers to a compound which contains 90% or more a component having a specific ethylene glycol chain length. Further, the term "does not have a chiral center" means that it is possible to superimpose the mirror images.

The heterobifunctional monodispersed polyethylene glycol of the invention is represented by formula (1).

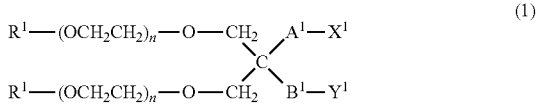

(1)

R[1] in formula (1) of the invention is a hydrocarbon group or a hydrogen atom. The number of carbon atoms of the hydrocarbon group is preferably 7 or less. Specific examples of the hydrocarbon group include a methyl group, an ethyl group, a propyl group, an isopropyl group, a tert-butyl group, a phenyl group and a benzyl group. A preferred embodiment of R[1] is a methyl group or a hydrogen atom, and more preferably a methyl group.

n in formula (1) of the invention represents a number of repeating units of monodispersed polyethylene glycol and is an integer of 3 to 72, preferably an integer of 4 to 48, more preferably an integer of 6 to 36, and particularly preferably an integer of 8 to 24.

In the specification, the atomic groups $X^1$ and $Y^1$ in formula (1) are different from each other and not particularly limited as long as they are atomic groups containing at least a functional group which reacts with a functional group present in a biofunctional molecule (for example, a physiologically active protein, a peptide, an antibody, a nucleic acid or a low-molecular drug), which is a target for modification by the heterobifunctional monodispersed polyethylene glycol, to from a covalent bond. Examples of the functional group include functional groups described, for example, in "Hennanson, G. T. Bioconjugate Techniques, 2nd ed.: Academic Press: San Diego, Calif., 2008", "Harris, J. M. Poly(Ethylene Glycol) Chemistry; Plenum Press: New York, 1992", and "PEGylated Protein Drugs: Basic Science and Clinical Applications; Veronese, F. M., Ed.; Birkhauser: Basel, Switzerland, 2009".

Among them, the functional groups included in $X^1$ and $Y^1$ are each independently preferably a functional group capable of reacting under mild conditions and with a high reaction efficiency with a functional group (for example, an amino group, a thiol group, an aldehyde group or a carboxyl group) present in a naturally occurring biofunctional molecule represented by protein or a functional group (for example, a maleimide group, a ketone group, an azide group or an alkynyl group) capable of artificially introducing into the biofunctional molecule described above. More specifically, it is preferably an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a 2-pyridyldithio group, an α-haloacetyl group, a hydroxy group, an alkynyl group, an allyl group, a vinyl group, an amino group, an oxyamino group, a hydrazide group, an azide group or a dibenzocyclooctyne (DBCO) group. Further, taking the reaction efficiency into consideration it is preferably an active ester group, an active carbonate group, a maleimide group, an α-haloacetyl group, an alkynyl group, an azide group or a dibenzocyclooctyne (DBCO) group.

In still more specifically, the functional groups included in $X^1$ and $Y^1$ are each independently an active ester group, an active carbonate group, an aldehyde group, an isocyanate group, an isothiocyanate group, an epoxy group, a maleimide group, a vinyl sulfone group, an acryl group, a sulfonyloxy group or a carboxy group in the case where the functional group present in the biofunctional molecule as the target for modification is an amino group; an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a 2-pyridyldithio group, an α-haloacetyl group, an alkynyl group, an allyl group or a vinyl group in the case where the functional group present in the biofunctional molecule as the target for modification is a thiol group; a thiol group, a hydroxy group, an amino group, an oxyamino group or a hydrazide group, in the case where the functional group present in the biofunctional molecule as the target for modification is an aldehyde group or a carboxy group; a thiol group or an azide group in the case where the functional group present in the biofunctional molecule as the target for modification is an alkynyl group; an alkynyl group or a dibenzocyclooctyne group in the case where the functional group present in the biofunctional molecule as the target for modification is an azide group; and a thiol group, a hydroxy group or an amino group in the case where the functional group present in the biofunctional molecule as the target for modification is a halogenated alkyl group, an alkylsulfonic acid eater or an arylsulfonic acid ester.

The term "active ester group" as referred to herein indicates an activated carboxy group represented by formula: —C(=O)-L, wherein L represents a leaving group. The leaving group represented by L includes a succinimidyloxy group, a phthalimidyloxy group, a 4-nitrophenoxy group, a 1-imidazolyl group, a pentafluorophenoxy group, a benzotriazol-1-yloxy group, a 7-azabenzotriazol-1-yloxy group and the like. The term "active carbonate" as referred to herein indicates an activated carbonate group represented by formula: —O—C(=O)-L, wherein L represents a leaving group same as that described above.

In a preferred embodiment of the invention, $X^1$ and $Y^1$ are each independently a group represented by group (I), group (II), group (III), group (IV), group (V) or group (VI). Group (I): Functional group capable of forming a covalent bond upon a reaction with an amino group of the biofunctional molecule (a), (b1), (b2), (c), (d), (e) and (f) shown below:
Group (II): Functional group capable of forming a covalent bond upon a reaction with a thiol group of the biofunctional molecule (a), (b1), (b2), (c), (d), (e), (f), (g), (h) and (l) shown below:
Group (III): Functional group capable of forming a covalent bond upon a reaction with an aldehyde group or a carboxy group of the biofunctional molecule (g), (i), (j), (k) and (o) shown below:
Group (IV): Functional group capable of forming a covalent bond upon a reaction with an alkynyl group of the biofunctional molecule (g), (i), (j), (k) and (n) shown below:
Group (V): Functional group capable of forming a covalent bond upon a reaction with an azide group of the biofunctional molecule (l) and (m) shown below
Group (VI): Functional group capable of forming a covalent bond upon a reaction with a halogenated alkyl group, an alkylsulfonic acid eater or an arylsulfonic acid ester of the biofunctional molecule (g), (i) and (o) shown below

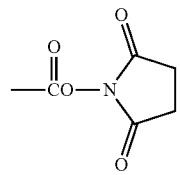
(a)

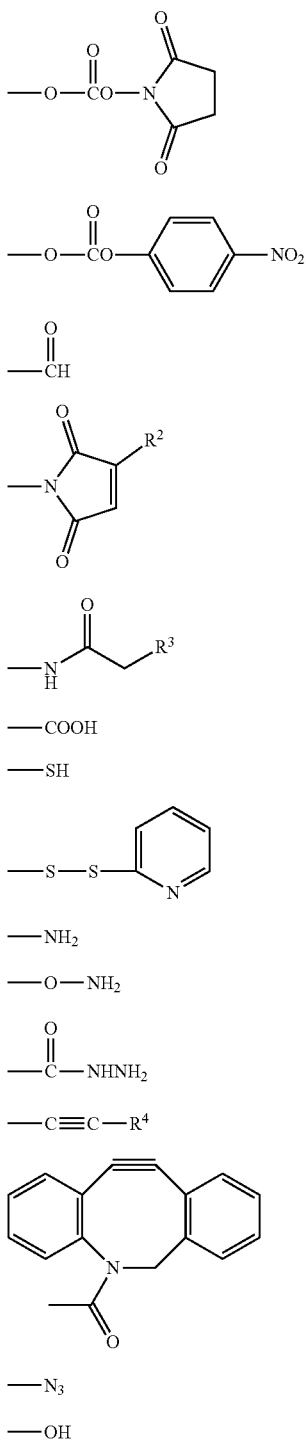

In the formulae above, R² and R⁴ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. R³ is a halogen atom selected from a chlorine atom, a bromine atom and an iodine atom.

As to preferred examples of a combination of the functional groups included in the atomic groups $X^1$ and $Y^1$ in formula (1), when the functional group included in $X^1$ is an active ester group or an active carbonate group, the functional group included in $Y^1$ is a group selected from a maleimide group, a vinyl sulfone group, an α-haloacetyl group, an alkynyl group and an azide group; when the functional group included in $X^1$ is an aldehyde group, the functional group included in $Y^1$ is a group selected from a maleimide group, a vinyl sulfone group, an alkynyl group and an azide group; when the functional group included in $X^1$ is a maleimide group, a vinyl sulfone group or an α-haloacetyl group, the functional group included in $Y^1$ is a group selected from an active ester group, an active carbonate group, an alkynyl group and an azide group; when the functional group included in $X^1$ is an alkynyl group or an azide group, the functional group included in $Y^1$ is a group selected from a maleimide group, a vinyl sulfone group, an α-haloacetyl group, an active ester group, an active carbonate group, an amino group, an oxyamino group and a hydroxy group; when the functional group included in $X^1$ is an amino group or an oxyamino group, the functional group included in $Y^1$ is a group selected from an alkynyl group, an azide group, a thiol group, a hydroxy group and a carboxy group; and when the functional group included in $X^1$ is a thiol group, a 2-pyridyldithio group or a hydroxy group, Y is a group selected from an amino group, an oxyamino group, an azide group and a carboxy group. More preferably, when the functional group included in $X^1$ is an active ester group or an active carbonate group, the functional group included in $Y^1$ is a group selected from a maleimide group, an α-haloacetyl group, an alkynyl group and an azide group; when the functional group included in $X^1$ is an aldehyde group, the functional group included in $Y^1$ is a group selected from a maleimide group, an α-haloacetyl group, an alkynyl group and an azide group; when the functional group included in $X^1$ is a maleimide group or an α-haloacetyl group, the functional group included in $Y^1$ is a group selected from an active ester group, an active carbonate group, an alkynyl group and an azide group; when the functional group included in $X^1$ is an alkynyl group or an azide group, the functional group included in $Y^1$ is a group selected from a maleimide group, an α-haloacetyl group, an active ester group, an active carbonate group, an amino group, an oxyamino group and a hydroxy group; when the functional group included in $X^1$ is an amino group or an oxyamino group, the functional group included in Y is a group selected from an alkynyl group, an azide group, a hydroxy group and a thiol group; and when the functional group included in $X^1$ is a thiol group, a 2-pyridyldithio group or a hydroxy group, the functional group included in $Y^1$ is a group selected from an amino group, an oxyamino group and an azide group.

$A^1$ in formula (1) of the invention is a divalent spacer between a quaternary carbon atom of the branched portion and $X^1$, and $B^1$ in formula (1) is a divalent spacer between the quaternary carbon atom of the branched portion and $Y^1$, and these are composed of a covalent bond, respectively. Specifically, $A^1$ represents -$L^1$-$(CH_2)_{m1}$—, -$L^1$-$(CH_2)_{m1}$-$L^2$-$(CH_2)_{m2}$— or a single bond, $L^1$ represents an ether bond, an amide bond, an urethane bond, a secondary amino group or a single bond, $L^2$ represents an ether bond, an amide bond or an urethane bond, and m1 and m2 represent each independently an integer of 1 to 5. $B^1$ represents -$L^3$-$(CH_2)_{m3}$—, -$L^3$-$(CH_2)_{m3}$-$L^4$-$(CH_2)_{m4}$— or a single bond, $L^3$ represents an amide bond or a single bond, $L^4$ represents an ether bond, an amide bond or an urethane bond, and m3 and m4 represent each independently an integer of 1 to 5.

Specific structures of $A^1$ and $B^1$ in formula (1) in a preferred embodiment of the invention and typical synthesis examples of the heterobifunctional monodispersed polyethylene glycol having $A^1$ and $B^1$ described above are described below, but the invention should not be construed as being limited thereto.

(A) In a preferred embodiment of the invention, $A^1$ in formula (1) is represented by —NHC(O)—$(CH_2)_{m1}$— or —NHC(O)—$(CH_2)_{m1}$-$L^2$-$(CH_2)_{m2}$—, $L^2$ is an ether bond, an amide bond or an urethane bond, and m1 and m2 are each independently an integer of 1 to 5, and $B^1$ is represented by —$(CH_2)_{m3}$— or —$(CH_2)_{m3}$-$L^4$-$(CH_2)_{m4}$—, $L^4$ is an ether bond, an amide bond or an urethane bond, and m3 and m4 are each independently an integer of 1 to 5. More preferably, $A^1$ is represented by —NHC(O)—$(CH_2)_{m1}$—, m1 is an integer of 1 to 5, and $B^1$ is represented by —$(CH_2)_{m3}$— or —$(CH_2)_{m3}$—O—$(CH_2)_{m4}$—, and m3 and m4 are each independently an integer of 1 to 5.

Typical example of synthesis of the heterobifunctional monodispersed polyethylene glycol described above includes the steps described below. Here, a compound into which a maleimide group and a p-nitrophenyl carbonate group are introduced as the functional groups is illustrated.

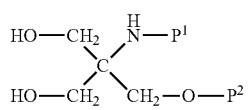

(in formula (3), $P^1$ is a protective group of an amino group, and $P^2$ is a protective group of a hydroxy group.)

The compound represented by formula (3) is subjected to a nucleophilic substitution reaction with an alkyl or aryl sulfonic acid ester of monomethyl monodispersed polyethylene glycol or a halide of monomethyl monodispersed polyethylene glycol in an anhydrous solvent in the presence of a strong base to obtain a compound represented by formula (4) shown below.

The "protective group" as referred to herein is a component which prevents or blocks a reaction of a specific functional group in the molecule under certain reaction conditions. The protective group varies depending on the kind of the functional group to be protected, the conditions to be used and the presence of the other functional group or protective group in the molecule. Specific examples of the protective group can be found in many general books and are described, for example, in "Wuts, P. G M.; Greene, T. W. Protective Groups in Organic Synthesis, 4th ed.; Wiley-Interscience: New York, 2007". Moreover, the functional group protected by the protective group can be reproduce the original functional group by deprotection using reaction conditions suitable for each of the protective groups, that is, causing a chemical reaction. The representative deprotection conditions of the protective group are described in the literature described above.

As to preferred combinations of the functional group to be protected and the protective group, when the functional group to be protected is an amino group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group. When the functional group to be protected is a hydroxy group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group.

When the functional group to be protected is a carboxy group, for example, an alkyl ester protective group and a silyl ester protective group are exemplified, and specific examples thereof include a methyl group, a 9-fluorenylmethyl group and a tert-butyldimethylsilyl group. When the functional group to be protected is a sulfanyl group, for example, a thioether protective group, a thiocarbonate protective group and a disulfide protective group are exemplified, and specific examples thereof include an S-2,4-dinitrophenyl group, an S-9-fluorenylmethyloxycarbonyl group and an S-tert-butyldisulfide group. Further, a bifunctional protective group capable of simultaneously protecting two functional groups of the same kinds or different kinds may be used. As to preferred combinations of the functional groups to be protected and the protective group, when the functional groups to be protected are two hydroxy groups, for example, a cyclic acetal protective group and a cyclic silyl protective group are exemplified, and specific examples thereof include a 2,2-dimethyl-1,3-dioxolane group, a 2,2-dimethyl-1,3-dioxane group, a 2-phenyl-1,3-dioxolane group, a 2-phenyl-1,3-dioxane group and a di-tert-butylsilylene group. When the functional groups to be protected are an amino group and a hydroxy group, for example, an oxazoline protective group is exemplified, and specific examples thereof include a 2-phenyloxazoline group.

The representative deprotection conditions of the protective group are described in the literature described above, and the reaction conditions suitable for each of the protective groups can be selected. However, in the case where the functional group contained in the structure is a functional group which does not inhibit the chemical reaction of other functional group even when the functional group is not protected by a protective group, it is not necessary to use a protective group.

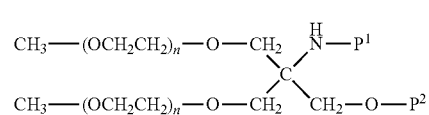

After deprotecting the protective group $P^1$ of the compound represented by formula (4) described above, the resulting compound is reacted with 6-maleimidohexanoic acid in the presence of a condensing agent to obtain a compound represented by formula (5) shown below. Here, when the reaction conditions in which the hydroxy group does not react with a reaction reagent of the amino group are selected, the protective group $P^2$ may also be deprotected simultaneously with the protective group $P^1$.

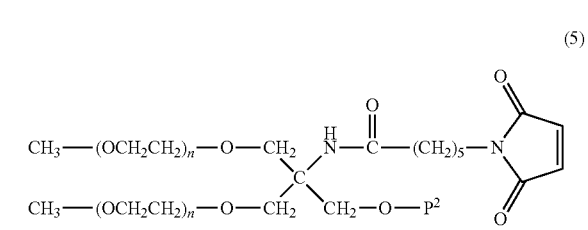

After deprotecting the protective group $P^2$ of the compound represented by formula (5) described above, the resulting compound is reacted with p-nitrophenyl chloroformate in the presence of a base to obtain a compound represented by formula (6) shown below.

(6)

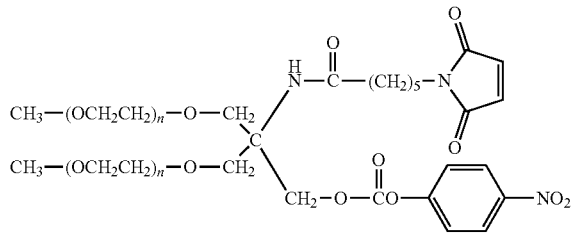

(B) In another preferred embodiment of the invention, $A^1$ in formula (1) is represented by —$CH_2$— or —$CH_2$-$L^2$-$(CH_2)_{m2}$—, $L^2$ is an ether bond, an amide bond or an urethane bond, and m2 is an integer of 1 to 5, and $B^1$ is represented by —$CH_2$— or —$CH_2$-$L^4$-$(CH_2)_{m4}$—, $L^4$ is an ether bond, an amide bond or an urethane bond, and m4 is an integer of 1 to 5. More preferably, $A^1$ is represented by —$CH_2$—NHC(O)—$(CH_2)_{m2}$—, m2 is an integer of 1 to 5, and $B^1$ is represented by —$CH_2$— or —$CH_2$—O—$(CH_2)_{m4}$—, and m4 is an integer of 1 to 5.

Typical example of synthesis of the heterobifunctional monodispersed polyethylene glycol described above includes the steps described below. Here, a compound into which an iodoacetamide group and an N-succinimidyl ester group are introduced as the functional groups is illustrated.

(7)

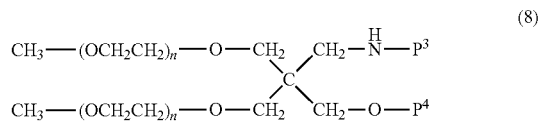

(in formula (7), $P^3$ is a protective group of an amino group, and $P^4$ is a protective group of a hydroxy group.)

The compound represented by formula (7) is subjected to a nucleophilic substitution reaction with an alkyl or aryl sulfonic acid ester of monomethyl monodispersed polyethylene glycol or a halide of monomethyl monodispersed polyethylene glycol in an anhydrous solvent in the presence of a strong base to obtain a compound represented by formula (8) shown below.

(8)

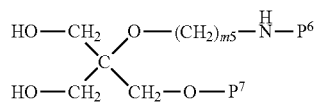

After deprotecting the protective group $P^4$ of the compound represented by formula (8) described above, the resulting compound is reacted with a carboxy group-protected body of 4-hydroxybutanoic acid in an anhydrous solvent in the presence of a base to obtain a compound represented by formula (9) shown below.

(9)

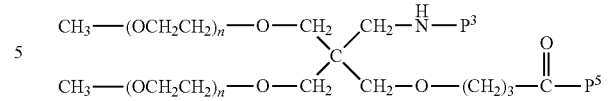

(in the formula, $P^5$ is a protective group of a carboxy group.)

After deprotecting the protective group $P^3$ of the compound represented by formula (9) described above, the resulting compound is reacted with iodoacetic anhydride to obtain a compound represented by formula (10) shown below.

(10)

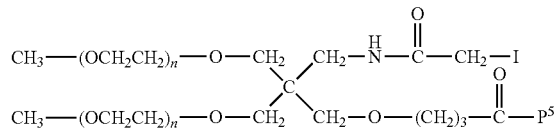

After deprotecting the protective group $P^5$ of the compound represented by formula (10) described above, the resulting compound is reacted with N-hydroxysuccinimide in the presence of a condensing agent to obtain a compound represented by formula (11) shown below.

(11)

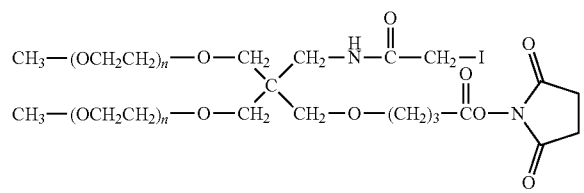

(C) In still another preferred embodiment of the invention, $A^1$ in formula (1) is represented by —O—$(CH_2)_{m1}$— or —O—$(CH_2)_{m1}$-$L^2$-$(CH_2)_{m2}$—, $L^2$ is an ether bond, an amide bond or an urethane bond, and m1 and m2 are each independently an integer of 1 to 5, and $B^1$ is represented by —$CH_2$— or —$CH_2$-$L^4$-$(CH_2)_{m4}$—, $L^4$ is an ether bond, an amide bond or an urethane bond, and m4 is an integer of 1 to 5. More preferably, $A^1$ is represented by —O—$(CH_2)_{m1}$—NHC(O)—$(CH_2)_{m2}$—, m1 and m2 are each independently an integer of 1 to 5, and $B^1$ is represented by —$CH_2$— or —$CH_2$—O—$(CH_2)_{m4}$—, and m4 is an integer of 1 to 5.

Typical example of synthesis of the heterobifunctional monodispersed polyethylene glycol described above includes the steps described below. Here, a compound into which a 2-pyridyldithio group and an N-succinimidyl carbonate group are introduced as the functional groups is illustrated.

(12)

HO—$CH_2$  O—$(CH_2)_{m5}$—N(H)—$P^6$
       \\C/
HO—$CH_2$  $CH_2$—O—$P^7$ (in formula (12), $P^6$ is a protective group of an amino group, and $P^7$ is a protective group of a hydroxy group.)

The compound represented by formula (12) is subjected to a nucleophilic substitution reaction with an alkyl or aryl sulfonic acid ester of monomethyl monodispersed polyethylene glycol or a halide of monomethyl monodispersed polyethylene glycol in an anhydrous solvent in the presence of a strong base to obtain a compound represented by formula (13) shown below.

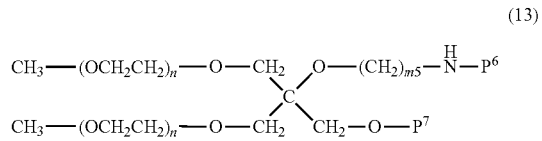

(13)

After deprotecting the protective group $P^6$ of the compound represented by formula (13) described above, the resulting compound is reacted with N-succinimidyl 3-(2-pyridyldithio)propionate to obtain a compound represented by formula (14) shown below.

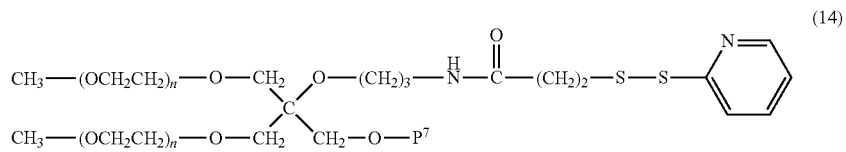

(14)

After deprotecting the protective group $P^7$ of the compound represented by formula (14) described above, the resulting compound is reacted with N,N-disuccinimidyl carbonate in the presence of a base to obtain a compound represented by formula (15) shown below.

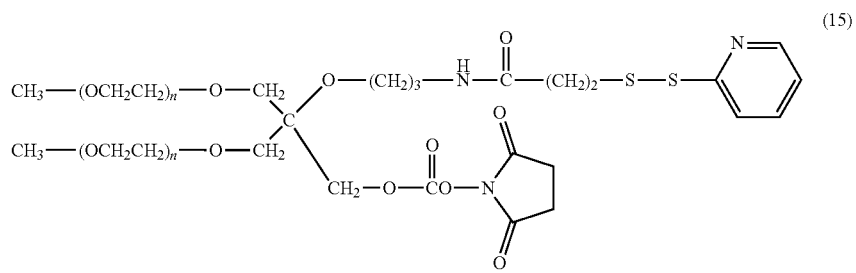

(15)

(D) In a further preferred embodiment of the invention, $A^1$ in formula (1) is represented by —C(O)NH—$(CH_2)_{m1}$— or —C(O)NH—$(CH_2)_{m1}$-$L^2$-$(CH_2)_{m2}$—, $L^2$ is an ether bond, an amide bond or an urethane bond, and m1 and m2 are each independently an integer of 1 to 5, and $B^1$ is represented by —$CH_2$— or —$CH_2$-$L^4$-$(CH_2)_{m4}$—, $L^4$ is an ether bond, an amide bond or an urethane bond, and m4 is an integer of 1 to 5. More preferably, $A^1$ is represented by —C(O)NH—$(CH_2)_{m1}$—, m1 is an integer of 1 to 5, and $B^1$ is represented by —$CH_2$— or —$CH_2$—O—$(CH_2)_{m4}$—, and m4 is an integer of 1 to 5.

Typical example of synthesis of the heterobifunctional monodispersed polyethylene glycol described above includes the steps described below. Here, a compound into which an azide group and a p-nitrophenyl carbonate group are introduced as the functional groups is illustrated.

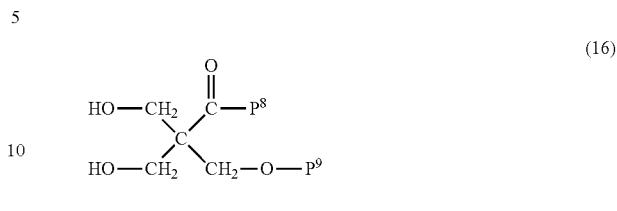

(16)

(in formula (16), $P^8$ is a protective group of a carboxy group, and $P^9$ is a protective group of a hydroxy group.)

The compound represented by formula (16) is subjected to a nucleophilic substitution reaction with an alkyl or aryl sulfonic acid ester of monomethyl monodispersed polyethylene glycol or a halide of monomethyl monodispersed polyethylene glycol in an anhydrous solvent in the presence of a strong base to obtain a compound represented by formula (17) shown below.

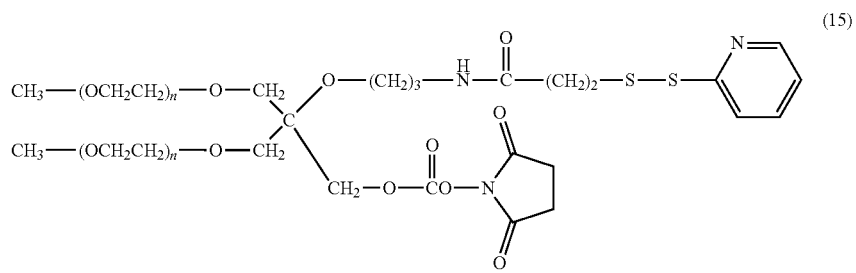

(17)

After deprotecting the protective group $P^8$ of the compound represented by formula (17) described above, the resulting compound is reacted with 3-azidepropylamine in the presence of a condensing agent to obtain a compound represented by formula (18) shown below.

(18)

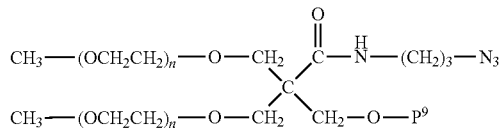

After deprotecting the protective group P⁹ of the compound represented by formula (18) described above, the resulting compound is reacted with p-nitrophenyl chloroformate in the presence of a base to obtain a compound represented by formula (19) shown below.

(19)

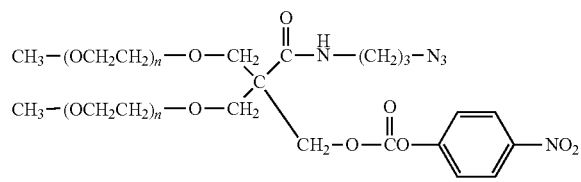

(E) In a still further preferred embodiment of the invention, $A^1$ in formula (1) is represented by —C(O)NH—$(CH_2)_{m1}$— or —C(O)NH—$(CH_2)_{m1}$-$L^2$-$(CH_2)_{m2}$—, $L^2$ is an ether bond, an amide bond or an urethane bond, and m1 and m2 are each independently an integer of 1 to 5, and $B^1$ is represented by —C(O)NH—$(CH_2)_{m3}$— or —C(O)NH—$(CH_2)_{m3}$-$L^4$-$(CH_2)_{m4}$—, $L^4$ is an ether bond, an amide bond or an urethane bond, and m3 and m4 are each independently an integer of 1 to 5. More preferably, $A^1$ is represented by —C(O)NH—$(CH_2)_{m1}$—, m1 is an integer of 1 to 5, and $B^1$ is represented by —C(O)NH—$(CH_2)_{m3}$—NHC(O)—$(CH_2)_{m4}$—, and m3 and m4 are each independently an integer of 1 to 5.

Typical example of synthesis of the heterobifunctional monodispersed polyethylene glycol described above includes the steps described below. Here, a compound into which a dibenzocyclooctyne (DBCO) group and a maleimide group are introduced as the functional groups is illustrated.

(20)

HO—CH₂  
　　　＼  
　　　　C—C—P¹⁰  
　　　／　‖  
HO—CH₂　O  
　　　　＼  
　　　　　C—N—(CH₂)₂—N—P¹¹  
　　　　　‖　H　　　　　H  
　　　　　O (in formula (20), $P^{10}$ is a protective group of a carboxy group, and $P^{11}$ is a protective group of an amino group.)

The compound represented by formula (20) is subjected to a nucleophilic substitution reaction with an alkyl or aryl sulfonic acid ester of monomethyl monodispersed polyethylene glycol or a halide of monomethyl monodispersed polyethylene glycol in an anhydrous solvent in the presence of a strong base to obtain a compound represented by formula (21) shown below.

(21)

CH₃—(OCH₂CH₂)ₙ—O—CH₂  
　　　　　　　　　　　＼  
　　　　　　　　　　　　C—C—P¹⁰  
　　　　　　　　　　　／‖  
　　　　　　　　　　　　O

CH₃—(OCH₂CH₂)ₙ—O—CH₂  
　　　　　　　　　　　＼  
　　　　　　　　　　　　C—N—(CH₂)₂—N—P¹¹  
　　　　　　　　　　　　‖ H　　　　　 H  
　　　　　　　　　　　　O

After deprotecting the protective group $P^{10}$ of the compound represented by formula (21) described above, the resulting compound is reacted with a dibenzocyclooctyne (DBCO)-amine derivative in the presence of a condensing agent to obtain a compound represented by formula (22) shown below.

(22)

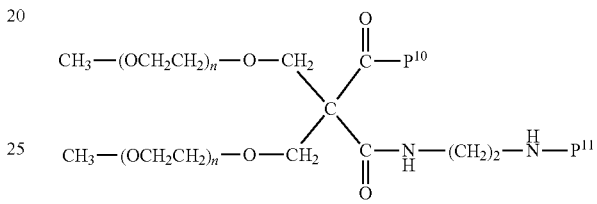

After deprotecting the protective group $P^{11}$ of the compound represented by formula (22) described above, the resulting compound is reacted with N-succinimidyl 3-maleimidopropionate to obtain a compound represented by formula (23) shown below.

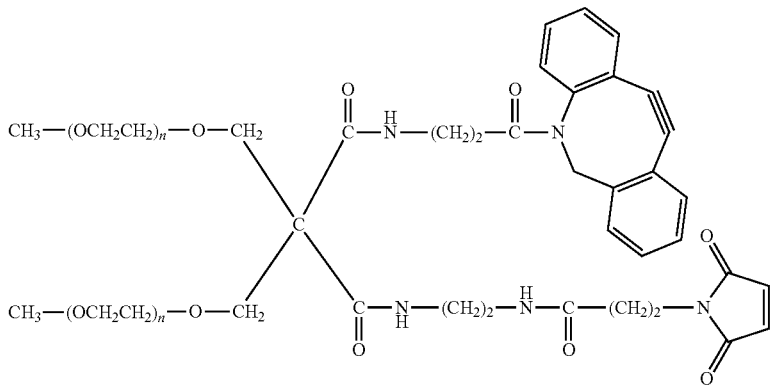

(23)

According to another aspect of the invention, an antibody-drug conjugate containing the heterobifunctional monodispersed polyethylene glycol represented by formula (2) is provided.

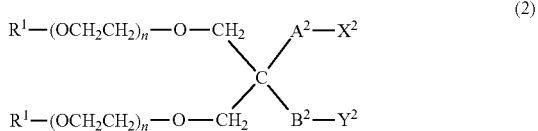

(2)

$R^1$ in formula (2) of the invention is a hydrocarbon group or a hydrogen atom. The number of carbon atoms of the hydrocarbon group is preferably 7 or less. Specific examples of the hydrocarbon group include a methyl group, an ethyl group, a propyl group, an isopropyl group, a tert-butyl group, a phenyl group and a benzyl group. A preferred embodiment of $R^1$ is a methyl group or a hydrogen atom, and more preferably a methyl group.

n in formula (2) of the invention represents a number of repeating units of monodispersed polyethylene glycol and is an integer of 3 to 72, preferably an integer of 4 to 48, more preferably an integer of 6 to 36, and particularly preferably an integer of 8 to 24.

In the specification, one of $X^2$ and $Y^2$ in formula (2) is an antibody and the other is a drug.

The term "antibody" as used in the specification is used in its broadest sense and specifically covers a monoclonal antibody, a polyclonal antibody, a dimer, a multimer, a multispecific antibody (for example, a bispecific antibody) and an antibody fragment, as far as it exhibits the desired biological activity (Miller, K. et al. J. Immunol. 2003, 170, 4854-4861).

The antibody can be a mouse antibody, a human antibody, a humanized antibody or a chimeric antibody, or can be derived from other species. The antibody is a protein generated by the immune system, which is capable of recognizing and binding to a specific antigen (Janeway, C.; Travers, P.; Walport, M.; Shlomchik, M. Immunobiology, 5th ed.; Garland Publishing: New York, 2001).

A target antigen generally has numerous binding sites (also called epitopes) recognized by CDRs on multiple antibodies. An antibody which specifically binds to a different epitope has a different structure. Therefore, one antigen may have more than one corresponding antibody. The antibody includes the full-length immunoglobulin molecule or an immunologically active portion of a full-length immunoglobulin molecule (that is, a molecule containing an antigen binding site which immunospecifically binds to an antigen of interest or part thereof). Such a target includes a cancer cell and a cell which generates an autoimmune antibody associated with an autoimmune disease, but it is not limited thereto. The immunoglobulin disclosed in the specification may be of any type (for example, IgG, IgE, IgM, IgD or IgA), class (for example, IgG1, IgG2, IgG3, IgG4, IgA1 or IgA2) or subclass thereof. The immunoglobulin may be derived from any species. However, in one embodiment, the immunoglobulin is of human origin, mouse origin or rabbit origin.

The polyclonal antibody is a heterogeneous population of antibody molecules, for example, that derived from the serum of immunized animal. The polyclonal antibody to an antigen of interest may be produced using known various procedures in the art. For example, in order to produce a polyclonal antibody, various host animals including, but not limited to, rabbit, mouse, rat and guinea pig, may be immunized by injection with an antigen of interest or derivative thereof. The immunological response may be increased by using various adjuvants including, but not limited to, Freund's (complete and incomplete) adjuvant, a mineral gel, for example, aluminum hydroxide, a surface active substance, for example, lysolecithin, a pluronic polyol, a polyanion, a peptide, an oil emulsion, keyhole limpet hemocyanin, dinitrophenol, and a potentially useful human adjuvant, for example, BCG (Bacille Calmett-Guerin) or *Corynebacterium parvum*, depending on the host species. Such adjuvants are also known in the art.

The monoclonal antibody is a homogeneous population of antibodies to a specific antigenic determinant (for example, a cell antigen (cancer or autoimmune cell antigen), a viral antigen, a microbial antigen, a protein, a peptide, a carbohydrate, a chemical substance, a nucleic acid or antigen-binding fragments thereof). A monoclonal antibody (mAb) to an antigen of interest may be prepared by using any technique known in the art. These include, but are not limited to, the hybridoma technique originally described by Kohler, G; Milstein, C. Nature 1975, 256, 495-497, the human B cell hybridoma technique (Kozbor, D. et al. Immunol. Today 1983, 4, 72-79) and the EBV-hybridoma technique (Cole, S. P. C. et al. Monoclonal Antibodies and Cancer Therapy; Alan R. Liss: New York, 1985, pp. 77-96). Such antibodies may be of any immunoglobulin class including IgG, IgM, IgE, IgA and IgD and any subclass thereof. The hybridoma producing the monoclonal antibody in the invention may be cultivated in vitro or in vivo.

The monoclonal antibody includes, but is not limited to, a human monoclonal antibody, a humanized monoclonal antibody, a chimeric monoclonal antibody and an antibody fragment. The human monoclonal antibody may be made by any of numerous techniques known in the art (see, for example, Teng, N. N. et al. Proc. Natl. Acad. Sci. USA. 1983, 80, 7308-7312, Kozbor, D. et al. Immunology Today 1983, 4, 72-79, Olsson L. et al. Meth. Enzymol. 1982, 92, 3-16, and U.S. Pat. Nos. 5,939,598 and 5,770,429). A recombinant antibody, for example, a chimeric monoclonal antibody or a humanized monoclonal antibody can be made using standard recombinant DNA techniques known in the art (see, for example, U.S. Pat. Nos. 4,816,567 and 4,816,397).

The immunogenicity of the antibody can also be reduced by the surface reconstruction (resurfacing) treatment of the antibody (see, U.S. Pat. No. 5,225,539 and European Patents 0239400, 0519596 and 0592106).

In one embodiment of the invention, the antibody may be a bispecific antibody. Methods for making the bispecific antibody are known in the art. Conventional production method of full-length bispecific antibody utilizes the simultaneous expression of two immunoglobulin heavy chain-light chain pairs in which the two chains have different specificities (see, Milstein, C. et al. Nature 1983, 305, 537-539). According to a different method, the bispecific antibody can also be produced by fusing an antibody variable domain with the desired binding specificity (antibody-antigen binding site) to an immunoglobulin constant domain sequence.

Other useful antibodies include fragments of antibodies, but are not limited to, F(ab')2 fragment, Fab' fragment, Fab fragment, Fvs, a single chain antibody (SCA) (for example, as described in U.S. Pat. No. 4,946,778, Bird, R. E. et al. Science 1988, 242, 423-442, Huston, J. S. et al. Proc. Natl. Acad. Sot USA 1988, 85, 5879-5883, and Ward, E. S. et al. Nature 1989, 334, 544-554), scFv, sc-Fv-Fc, FvdsFv, minibody, diabody, triabody, tetrabody, and any other molecule containing CDR and having the same specificity as the antibody, for example, a domain antibody.

In a preferred embodiment of the invention, a known antibody for the treatment or prevention of cancer may be used. All target proteins including any target protein whose expression is correlated with expression on cells of a cancer, cell proliferative disorder or tumor can be targeted by an antibody.

In a preferred embodiment of the invention, the antibody is useful for the treatment of cancer. Examples of the antibody useful for the treatment of cancer include, but are not limited to, RITUXAN (registered trademark) (Genentech Inc.) which is a chimeric anti-CD20 monoclonal antibody for the treatment of patient with non-Hodgkin's lymphoma, OVAREX (AltaRex Corp.) which is a mouse antibody for the treatment of ovarian cancer, PANOREX (Glaxo Wellcome Inc.) which is a mouse IgG2a antibody for the treatment of colorectal cancer, CETUXIMAB ERBITUX (ImClone Systems Inc.) which is an anti-EGFR IgG chimeric antibody for the treatment of epidermal growth factor positive cancer, for example, head cancer or neck cancer, VITAXIN (MedImmune Inc.) which is a humanized antibody for the treatment of sarcoma, CAMPATH I/H (Leukosite Inc.) which is a humanized IgG1 antibody for the treatment of chronic lymphocytic leukemia (CLL), Smart M195 (Protein Design Labs Inc.) which is a humanized anti-CD33 IgG antibody for the treatment of acute myeloid leukemia (AML), LYMPHOCIDE (Immunomedics Inc.) which is a humanized anti-CD22 IgG antibody for the treatment of non-Hodgkin's lymphoma, Smart ID 10 (Protein Design Labs Inc.) which is a humanized anti-HLA-DR antibody for the treatment of non-Hodgkin's lymphoma, Oncolym (Techniclone Inc.) which is a radiolabeled mouse anti-HLA-Dr10 antibody for the treatment of non-Hodgkin's lymphoma, ALLOMUNE (BioTransplant Inc.) which is a humanized anti-CD2 mAb for the treatment of Hodgkin's disease or non-Hodgkin's lymphoma, AVASTIN (Genentech Inc.) which is an anti-VEGF humanized antibody for the treatment of lung cancer and colorectal cancer, Epratuzamab (Immunomedics Inc. and Amgen Inc.) which is an anti-CD22 antibody for the treatment of non-Hodgkin's lymphoma, and CEAcide (Immunomedics Inc.) which is a humanized anti-CEA antibody for the treatment of colorectal cancer.

In a preferred embodiment of the invention, the antibody is an antibody to the following antigens: CA125, CA15-3, CA19-9, L6, Lewis Y, Lewis X, alpha fetoprotein, CA242, placental alkaline phosphatase, prostate specific membrane antigen, EphB2, TMEFF2, prostatic acid phosphatase, epidermal growth factor, MAGE-1, MAGE-2, MAGE-3, MAGE-4, anti-transferrin receptor, p97, MUC1-KLH, CEA, gp 100, MART 1, prostate specific antigen, IL-2 receptor, CD20, CD52, CD33, CD22, human chorionic gonadotropin, CD38, CD40, mucin, P21, MPG and Neu oncogene product.

Some specific useful antibodies include, but are not limited to, mAb to the CD40 antigen, for example, BR96 mAb (Trail, P. A. et al. Science 1993, 261, 212-215), BR64 (Trail, P. A. et al. Cancer Research 1997, 57, 100-105) or S2C6 mAb (Francisco, J. A. et al. Cancer Res. 2000, 60, 3225-3231) or other anti-CD40 antibodies, for example, as those disclosed in U.S. Patent Application Publication Nos. 2003/0211100 and 2002/0142358, mAb to the CD70 antigen, for example, 1F6 mAb and 2F2 mAb, and mAb to the CD30 antigen, for example, AC10 (Bowen, M. A. et al. J. Immunol. 1993, 151, 5896-5906, Wahl, A. F. et al. Cancer Res. 2002, 62(13), 3736-3742) or MDX-0060 (U.S. Patent Application Publication No. 2004/0006215).

The drug which can be used in the invention includes a chemotherapeutic agent. The chemotherapeutic agent is a compound useful in the treatment of cancer Examples of the chemotherapeutic agent include the followings: alkylating agents, for example, thiotepa or cyclophosphamide (CYTOXAN (trademark)); alkyl sulfonates, for example, busulfan, improsulfan or piposulfan; aziridines for example, benzodopa, carboquone, meturedopa or uredopa; ethyleneimines and methylamelamines including altretamine, triethylenemelamine, triethylenephosphoramide, triethylenethiophosphoramide and trimethylolomelamine; acetogenins (particularly bullatacin and bullatacinone); camptothecin (including synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including synthetic analogs KW-2189 and CBI-TMI; eleutherobin; pancratistatin; sarcodictyin; spongistatin; nitrogen mustards, for example, chlorambucil, chlornaphazine, cholophosphamide, estramustine, ifosfamide, mechlorethamine, mechlorethamine oxide hydrochloride, melphalan, novembichin, phenesterine, prednimustine, trofosfamide or uracil mustard; nitrosoureas, for example, carmustine, chlorozotocin, fotemustine, lomustine, nimustine or ranimustine; antibiotics, for example, enediyne antibiotics (for example, calicheamicin, particularly calicheamicin gamma 1 and calicheamicin theta 1, see, for example, Angew Chem Intl. Ed. Engl. 33:183-186 (1994); dynemicin (including dynemicin A); esperamicin; or neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, for example, methotrexate or 5-fluorouracil (5-FU); folic acid analogs, for example, demopterin, methotrexate, pteropterin or trimetrexate; purine analogs, for example, fludarabine, 6-mercaptopurine, thiamiprine or thioguanine; pyrimidine analogs, for example, ancitabine, azacitidine, 6-azauridine, carmofur, cytarabine, dideoxyuridine, doxifluridine, enocitabine, floxuridine or 5-FU; androgens, for example, calusterone, dromostanolone propionate, epitiostanol, mepitiostane or testolactone; anti-adrenals, for example, aminoglutethimide, mitotane or trilostane; folic acid replenisher, for example, frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; epothilone; etogiucid; gallium nitrate; hydroxy urea; lentinan; lonidamine; maytansinoids, for example, maytansine or ansamitocins; mitoguazone; mitoxantrone; mopidamol; nitracrine; pentostatin; phenamet; pirarubicin; podophyllinic acid; 2-ethylhydrazide; procarbazine; PSK (registered trademark); razoxane; rhizoxin; sizofiran: spirogermanium; tenuazonic acid; triaziquone; 2,2',2"-trichlorotriethylamine; trichothecenes (particularly T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiotepa: taxoids, for example, paclitaxel (TAXOL (registered trademark), Bristol-Myers Squibb Oncology) or doxetaxel (TAXOTERE (registered trademark), Rhone-Poulenc Rorer); chlorambucil; gemcitabine; 6-thioguanine; mercaptopurine; methotrexate; platinum analogs, for example, cisplatin or carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of those described above. Anti-hormonal agents which act to regulate or inhibit hormone action on tumors, for example, anti-estrogen drugs including, for example, tamoxifen, raloxifene, 4(5)-imidazoles inhibiting aromatase, 4-hydroxytamoxifen, trioxifene, keoxifene, LY 117018, onapristone and toremifene (Fareston); and anti-androgen drugs, for example, flutamide, nilutamide, bicalutamide, leuprolide or goserelin; siRNA, and pharmaceutically acceptable salts, acids or derivatives of any of those described above are also included in the definition. Other chemotherapeutic agents which can be used with the invention are disclosed in U.S. Patent Application Publication Nos. 2008/0171040 and 2008/0305044, all of which are incorporated by reference in their entirety herein.

In a preferred embodiment of the invention, the chemotherapeutic agent is a low molecular drug. The low molecular drug has a molecular weight preferably from 100 to 1,500, more preferably from 120 to 1,200, and still more preferably from 200 to 1,000. Typically as the low molecular drug, organic, inorganic or organometallic compounds having a molecular weight of less than about 1,000 is widely used. The low molecular drugs of the invention also include oligopeptides and other biomolecules each having a molecular weight of less than about 1,000. The low molecular drugs are well characterized in the art, for example, especially in WO 05/058367, EP-A-85901495, EP-A-8590319 and U.S. Pat. No. 4,956,303, all of which are incorporated by reference in their entirety herein.

A preferred low molecular drug of the invention is a low molecular drug capable of being linked to the antibody. The invention includes known drugs as well as those which may become known. Particularly preferred low molecular drugs include a cytotoxic agent.

Preferred cytotoxic agents include maytansinoids, CC-1065 analogues, morpholinos, doxorubicins, taxanes, cryptophycins, epothilones, calicheamicins, auristatins and pyrrolobenzodiazepine dimers.

The antibody-drug conjugate containing the heterobifunctional monodispersed polyethylene glycol represented by formula (2) of the invention can be prepared by bonding an antibody and a drug by using the heterobifunctional monodispersed polyethylene glycol represented by formula (1). The preparation method of the antibody-drug conjugate represented by formula (2) may be a method in which the heterobifunctional monodispersed polyethylene glycol represented by formula (1) is bonded to a drug and then bonded to an antibody or a method in which the heterobifunctional monodispersed polyethylene glycol represented by formula (1) is bonded to an antibody and then bonded to a drug. Further, purification may be performed after either one of the antibody or the drug is bonded or may be performed after both the antibody and the drug are bonded.

A compound in which the heterobifunctional monodispersed polyethylene glycol represented by formula (1) is bonded to the drug can be purified by a purification means, for example, column chromatography, extraction, recrystallization, adsorbent treatment, reprecipitation or supercritical extraction. Further, a compound in which the heterobifunctional monodispersed polyethylene glycol represented by formula (1) is bonded to the antibody and an antibody-drug conjugate in which the heterobifunctional monodispersed polyethylene glycol represented by formula (1) is bonded to both the antibody and the drug can be purified by a purification means, for example, column chromatography, extraction or adsorbent treatment.

The number of the drugs bonded to the antibody through the heterobifunctional monodispersed polyethylene glycol represented by formula (1) of the invention is defined by an average number of drugs per antibody. The number of the drugs is preferably from 1 to 20, more preferably from 2 to 16, still more preferably from 3 to 12, and particularly preferably from 4 to 8.

The number of drugs per antibody in ADC can be determined by a method known to those skilled in the art, for example, ultraviolet/visible spectroscopy, mass spectrometry, ELISA method, electrophoresis, HPLC or a combination of these methods.

$A^2$ in formula (2) of the invention is a divalent spacer between a quaternary carbon atom of the branched portion and $X^2$, and $B^2$ in formula (2) is a divalent spacer between the quaternary carbon atom of the branched portion and $Y^2$, and these are composed of a covalent bond, respectively.

Specifically, $A^2$ represents -$L^1$-$(CH_2)_{m1}$-$L^5$-, -$L^2$-$(CH_2)_{m1}$-$L^2$-$(CH_2)_{m2}$-$L^5$- or a single bond, $L^1$ represents an ether bond, an amide bond, an urethane bond, a secondary amino group or a single bond, $L^2$ represents an ether bond, an amide bond or an urethane bond, and m1 and m2 represent each independently an integer of 1 to 5. Here, $L^5$ represents an atomic group formed upon a reaction between the functional group included in $X^1$ of the heterobifunctional monodispersed polyethylene glycol represented by formula (1) and a functional group present in the antibody or the drug, and is preferably an amide bond, an urethane bond, a thioether bond, a disulfide bond, a carbonate bond, an ester bond, an ether bond, a 1H-1,2,3-triazole-1,4-diyl structure, a secondary amino group, a hydrazide group, an oxyamide group, or a hydrocarbon group containing any of them.

Further, $B^2$ represents -$L^3$-$(CH_2)_{m3}$-$L^6$-, -$L^3$-$(CH_2)_{m3}$-$L^4$-$(CH_2)_{m4}$-$L^6$- or a single bond, $L^3$ represents an amide bond or a single bond, $L^4$ represents an ether bond, an amide bond or an urethane bond, and m3 and m4 represent each independently an integer of 1 to 5. Here, $L^6$ represents an atomic group formed upon a reaction between the functional group included in $Y^1$ of the heterobifunctional monodispersed polyethylene glycol represented by formula (1) and a functional group present in the antibody or the drug, and is preferably an amide bond, an urethane bond, a thioether bond, a disulfide bond, a carbonate bond, an ester bond, an ether bond, a 1H-1,2,3-triazole-1,4-diyl structure, a secondary amino group, a hydrazide group, an oxyamide group, or a hydrocarbon group containing any of them.

EXAMPLES

The invention will be described more specifically with reference to the examples, but the invention should not be construed as being limited thereto.

In $^1$H-NMR analysis, JNM-ECP400 or JNM-ECA600 manufactured by JEOL DATUM Ltd. was used. For the measurement, a tube of 5 mm φ was used, and tetramethylsilane (TMS) was used as an internal standard substance in the case where a deuterated solvent was $CDCl_3$ or $CD_3OD$.

Example 1

Into a 500 mL four-necked flask equipped with a thermometer, a nitrogen inlet tube, a stirrer, a Dean-stark tube and a condenser tube were charged trishydroxymethylaminomethane (30.3 g, 250 mmol), sodium carbonate (5.30 g, 50 mmol), dehydrated methanol (237 g) and benzonitrile (5.15 g, 50 mmol), and the reaction was performed at 65° C. for 24 hours. The reaction mixture was filtered, the solvent was distilled off under a reduced pressure, then the residue was dissolved by adding isopropyl alcohol and dichloromethane, and the solution was washed with an aqueous 10% by weight sodium chloride solution. The organic layer was dried over anhydrous sodium sulfate, filtered, and the solvent was distilled off under a reduced pressure. The residue was dissolved in THF, and crystallization was performed by adding hexane, followed by filtration to obtain a compound of formula (24).

$^1$H-NMR ($CDCl_3$, internal standard TMS); δ (ppm):
3.06 (2H, brs, —O$\underline{H}$),
3.65-3.81 (4H, dd, >C(C$\underline{H}_2$OH)$_2$),
4.38 (2H, s, —CNO—C$\underline{H}_2$—),
7.32-7.83 (5H, m, arom.$\underline{H}$)

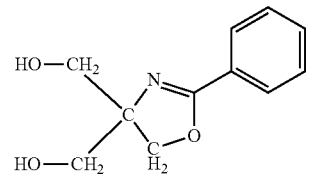

Example 2

Into a 100 mL three-necked flask equipped with a thermometer, a nitrogen inlet tube, a stirrer, a Dean-stark tube and a condenser tube were charged dodecaethylene glycol monomethyl ether (10.4 g, 18.5 mmol), toluene (52.0 g), triethylamine (2.44 g, 24.1 mmol) and methanesulfonyl chloride (2.34 g, 20.4 mmol), and the reaction was performed at 40° C. for 3 hours. The reaction solution was diluted by adding dichloromethane and then washed with water, and the organic layer was dried over anhydrous magnesium sulfate. After filtration, the solvent was distilled off under a reduced pressure to obtain a compound of formula (25).

$^1$H-NMR ($CDCl_3$, internal standard TMS); δ (ppm):
3.08 (3H, s, —O—$SO_2$—C$\underline{H}_3$),
3.38 (3H, s, —O—C$\underline{H}_3$),
3.45-3.85 (46H, m, $CH_3$—O—(C$\underline{H}_2$C$\underline{H}_2$O)$_{11}$—C$\underline{H}_2$C$\underline{H}_2$—O—$SO_2$—$CH_3$),
4.38 (2H, m, —C$\underline{H}_2$—O—$SO_2$—$CH_3$)

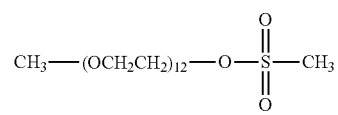

Example 3

Into a 50 mL three-necked flask equipped with a thermometer, a nitrogen inlet tube, a stirrer, a Dean-stark tube and a condenser tube were charged the compound of formula (24) (0.21 g, 1.01 mmol), dehydrated THF (7.70 g), the compound of formula (25) (2.46 g, 3.84 mmol), 1M tert-butoxy potassium THF solution (3.72 g. 4.04 mmol), and the reaction was performed at 50° C. for 4 hours. After adding dichloromethane and an aqueous 25% by weight sodium chloride solution, water washing was performed, and the organic layer was dried over anhydrous sodium sulfate. After filtration, the solvent was distilled off under a reduced pressure to obtain a compound of formula (26).

$^1$H-NMR ($CDCl_3$, internal standard TMS); δ (ppm):
3.38 (6H, s, —O—C$\underline{H}_3$),
3.40-3.75 (100H, m, >C(C$\underline{H}_2$O)$_2$—, —O—(C$\underline{H}_2$C$\underline{H}_2$O)$_{12}$—, —CNO—C$\underline{H}_2$—),
4.36 (2H, s, —CNO—C$\underline{H}_2$—),
7.37-7.94 (5H, m, arom.$\underline{H}$)

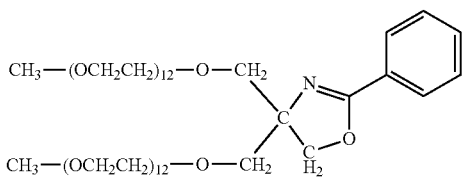

(26)

Example 4

To a 100 mL three-necked flask equipped with a thermometer, a nitrogen inlet tube, a stirrer, a Dean-stark tube and a condenser tube were added the compound of formula (26) (1.13 g, 0.877 mmol) and distilled water (31.1 g) to be dissolved. After adding 85% phosphoric acid (0.43 mL) to adjust pH to 1.5, the reaction was performed at 50° C. for 3 hours. After adding an aqueous 400 g/L sodium hydroxide solution (5.58 mL) with cooling, the reaction was performed at 50° C. for 6 hours. Subsequently, 6N hydrochloric acid was added to adjust pH to 2.0 and then toluene and chloroform were added thereto to perform washing. Sodium chloride was added so as to provide an aqueous 25% sodium chloride solution and then, using an aqueous 400 g % L sodium hydroxide solution pH was adjusted to 12.5. Extraction was performed by using toluene, and the extract was dried over anhydrous sodium sulfate. After filtration, the solvent was distilled off under a reduced pressure to obtain a compound of formula (27).

$^1$H-NMR (CDCl$_3$, internal standard TMS); δ (ppm):
3.08 (1H, brs, —OH),
3.38 (6H, s, —O—CH$_3$),
3.40-3.80 (102H, m, >C(CH$_2$O)$_2$—, —O—(CH$_2$CH$_2$O)$_{12}$—, >CNH$_2$—CH$_2$—OH)

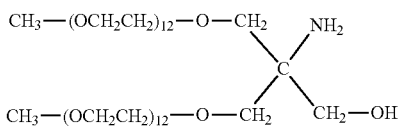

(27)

Example 5

Into a 50 mL three-necked flask equipped with a thermometer, a nitrogen inlet tube, a stirrer, a Dean-stark tube and a condenser tube were charged the compound of formula (27) (0.800 g, 0.663 mmol), 6-maleimidohexanoic acid (0.161 g, 0.762 mmol), DMT-MM (0.263 g, 0.762 mmol), acetonitrile (8.00 g) and triethylamine (0.081 g, 0.796 mmol), and the reaction was performed at 25° C. for 7 hours. Citrate buffer of pH 3.0 (9.60 g) was added thereto and then washing was performed by using toluene. Extraction was performed by using chloroform, and the organic layer was washed with an aqueous 10% sodium chloride solution. The organic layer was dried over anhydrous magnesium sulfate, filtrated, and the solvent was distilled off under a reduced pressure to obtain a compound of formula (28).

$^1$H-NMR (CDCl$_3$, internal standard TMS); δ (ppm):
1.31 (2H, m, —CH$_2$CH$_2$CH$_2$—CONH—),
1.62 (4H, m, —CH$_2$CH$_2$CH$_2$CH$_2$—CONH—),
2.18 (2H, t, —CH$_2$—CONH—),
3.38 (6H, s, —O—CH$_3$),
3.40-3.85 (104H, m, >C(CH$_2$O)$_2$—, —O—(CH$_2$CH$_2$O)$_{12}$—, >CNH—CH$_2$—OH, —CH$_2$- maleimide),
4.62 (1H, t, —OH),
6.23 (1H, s, —CH$_2$—CONH—),
6.69 (2H, s, -maleimide)

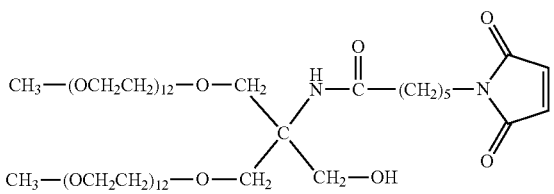

(28)

Example 6

To a 4-mL screw tube containing a stirrer were added the compound of formula (28) (0.050 g, 0.036 mmol), N-methylmorpholine (0.036 g, 0.357 mmol), Bis(4-nitrophenyl) carbonate (0.087 g, 0.286 mmol) and dehydrated acetonitrile (0.281 g), and the reaction was performed at 25° C. for 10 hours in a nitrogen atmosphere. Distilled water (0.018 g, 1.00 mmol) and N-methylmorpholine (0.022 g, 0.214 mmol) were added thereto, the mixture was stirred at 25° C. for 6 hours and then diluted by using dichloromethane. The mixture was washed by using citrate buffer of pH 3.0, borate buffer of pH 10.0 and then an aqueous 25% sodium chloride solution. The organic layer was dried over anhydrous sodium sulfate, filtered, and the solvent was distilled off under a reduced pressure to obtain a compound of formula (29).

$^1$H-NMR (CDCl$_3$, internal standard TMS); δ (ppm):
1.31 (2H, m, —CH$_2$CH$_2$CH$_2$—CONH—),
1.59 (4H, m, —CH$_2$CH$_2$CH$_2$CH$_2$—CONH—),
2.16 (2H, t, —CH$_2$—CONH—),
3.38 (6H, s, —O—CH$_3$),
3.40-3.85 (102H, m, >C(CH$_2$O)$_2$—, —O—(CH$_2$CH$_2$O)$_{12}$—, —CH$_2$-maleimide),
4.70 (1H, s, >CNH—CH$_2$—OCOO—),
6.02 (1H, s, —CH$_2$—CONH—),
6.69 (2H, s, -maleimide),
7.35-8.35 (4H, m, arom.H)

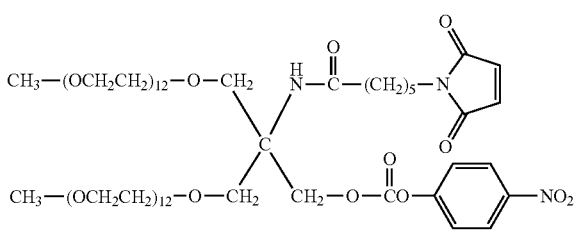

(29)

Example 7

To a 4-mL screw tube containing a stirrer were added doxorubicin hydrochloride (4.08 mg, 7.03 μmol), N,N-diisopropylamnine (1.98 mg, 14.7 μmol)), N,N-dimethylformamide and the compound of formula (29) (10.0 mg, 6.39

μmol), and the reaction was performed for 4 hours. After dilution with dichloromethane, the mixture was washed by using an aqueous 5% by weight sodium dihydrogen phosphate 12-hydrate solution and then using ion exchange water. The organic layer was dried over anhydrous sodium sulfate, filtered, and the solvent was distilled off under a reduced pressure to obtain a drug-linker compound of formula (30).

$^1$H-NMR (CD$_3$Cl, internal standard TMS); δ (ppm):
1.23-1.31 (5H, m), 1.55-1.65 (4H, m), 1.75-1.88 (2H, m),
2.08 (2H, t), 2.14-2.39 (2H, m), 2.88 (1H, dd),
3.02 (1H, s), 3.18 (2H, dd), 3.38 (3H, s),
3.41-3.90 (110H, m), 4.03-4.06 (1H, m), 4.09 (3H, s),
4.12-4.14 (1H, m), 4.22-4.47 (1H, m), 4.65 (1H, s),
4.77 (2H, d), 5.33 (1H, s), 5.42-5.44 (1H, m),
5.53 (1H, s), 6.16 (1H, s), 6.69 (2H, s),
7.41 (1H, d), 7.80 (1H, t), 8.06 (1H, d)

Example 8

As to the drug-linker compound of formula (30) obtained in Example 7, HPLC measurement was performed using a hydrophobic interaction chromatography (HIC) column under the measurement conditions described below. A chart of the measurement results was shown in FIG. 1.

HPLC apparatus: Alliance (Waters)
Column: TSKgel Butyl-NPR (4.6×35 mm, 2.5 μm; Tosoh Corp.)
Flow rate: 0.8 mL/minute,
Analysis time: 45 minutes,
Column temperature: 25° C.,
Injection amount: 100 μL,
Detector: photodiode array (measurement wavelength: 200-600 nm)
Mobile phase A: 50 mM sodium phosphate buffer solution (pH 7.0) containing 1.5 M ammonium sulfate
Mobile phase B: A mixed solution containing 80% of 50 mM sodium phosphate buffer solution (PH 7.0) and 20% of isopropyl alcohol
Gradient program: 0% to 0% (0 minute to 2.5 minutes), 0% to 100% (2.5 minutes to 35 minutes), 100% to 0% (35.1 minutes to 45 minutes)

Example 9

Monoclonal anti-interleukin-1 beta antibody produced in mouse (0.500 mg, Sigma-Aldrich) was dissolved in phosphate buffered saline (PBS, 0.500 mL). The solution (0.048 mL) was put into a 0.5 mL polyethylene tube, 50.0 mM of ethylenediamine tetraacetic acid (EDTA, 0.006 mL) and an aqueous 0.800 mM tris(2-carboxymethyl)phosphine hydrochloride (TCEP) solution (0.006 mL; 15 equivalents to the antibody) were added thereto, and the mixture was shaken at 37° C. for one hour. To the solution was added a solution containing N,N-dimethylacetamide and 2.50 mM of the compound of formula (30) (0.007 mL; 53 equivalents to the antibody), and the mixture was further shaken at 20° C. for one hour. An aqueous 2.50 mM N-acetyl cysteine (0.007 mL; 53 equivalents to an antibody) solution was added thereto, and the resulting mixture was further shaken at 20° C. for one hour. The resulting solution was filled in a NAP-5 column (GE Healthcare Life Science) equilibrated by using PBS (10 mL) and eluted with PBS to separate an antibody fraction.

Example 10

An average binding number per antibody in an antibody-drug conjugate can be calculated by measuring the UV absorbance of an aqueous solution of the antibody-drug conjugate at two wavelengths of 280 nm and 495 nm and then performing the calculation shown below.

Since the total absorbance at a certain wavelength is equal to the sum of the absorbance of all the absorbing chemical species present in the system (additivity of absorbance), assuming that there is no change in the molar extinction coefficient of the antibody and the drug before and after the conjugation reaction between the antibody and the drug, the antibody concentration and the drug concentration in the antibody-drug conjugate are represented by the relational expression shown below.

$$A_{280}=A_{D,280}+A_{A,280}=\varepsilon_{D,280}C_D+\varepsilon_{A,280}C_A \qquad \text{Formula (i)}$$

$$A_{495}=A_{D,495}+A_{A,495}=\varepsilon_{D,495}C_D+\varepsilon_{A,495}C_A \qquad \text{Formula (ii)}$$

(30)

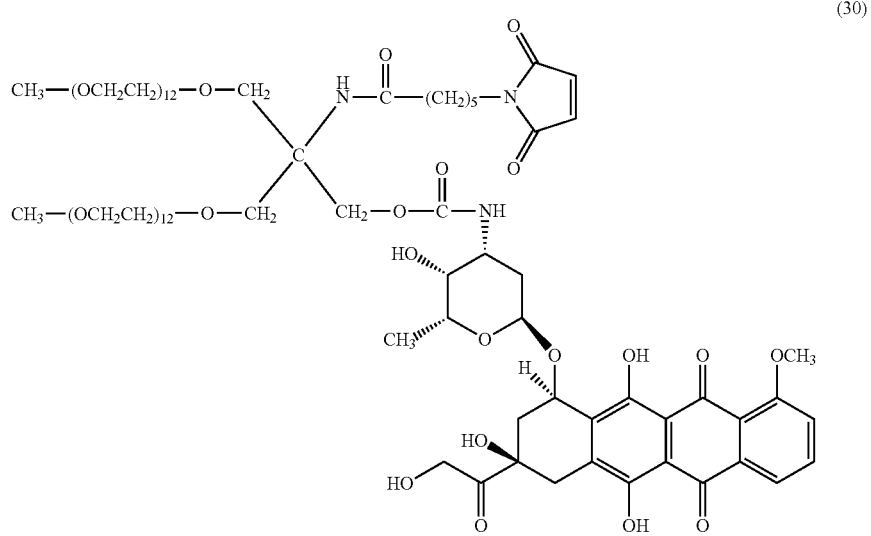

Here, $A_{280}$ indicates the absorbance of the aqueous solution of the antibody-drug conjugate at 280 nm, $A_{495}$ indicates the absorbance of the aqueous solution of the antibody-drug conjugate at 495 nm, $\varepsilon_{A, 280}$ indicates the absorbance of the antibody at 280 nm, $A_{A, 495}$ indicates the absorbance of the antibody at 495 nm, $A_{D, 280}$ indicates the absorbance of the drug-linker compound at 280 nm, $A_{D, 495}$ indicates the absorbance of the drug-linker compound at 495 nm, $\varepsilon_{A, 280}$ indicates the molar extinction coefficient of the antibody at 280 nm, $\varepsilon_{A, 495}$ indicates the molar extinction coefficient of the antibody at 495 nm, $\varepsilon_{D, 280}$ indicates the molar extinction coefficient of the drug-linker compound at 280 nm, $\varepsilon_{D, 495}$ indicates the molar extinction coefficient of the drug-linker compound at 495 nm, $C_A$ indicates the antibody concentration in the antibody-drug conjugate, and $C_D$ indicates the drug concentration in the antibody-drug conjugate.

Here, for $\varepsilon_{A, 280}$, $\varepsilon_{A, 495}$, $\varepsilon_{D, 280}$ and $\varepsilon_{D, 495}$, values previously prepared (estimated values or measured values obtained from UV measurement of the compound) are used. $\varepsilon_{A, 495}$ is ordinarily 0. $\varepsilon_{D, 280}$ and $\varepsilon_{D, 495}$ can be obtained by measuring the absorbance of a solution in which the drug-linker compound used is dissolved in a certain molar concentration and calculating according to Lambert-Beer law (absorbance=molar concentration×molar extinction coefficient×cell optical path length). $C_A$ and $C_D$ can be obtained by measuring $A_{280}$ and $A_{495}$ of the aqueous solution of the antibody-drug conjugate and substituting these values into formula (i) and formula (ii) to solve the simultaneous equations. Further, the average drug binding number per antibody can be obtained by dividing $C_D$ by $C_A$.

As a result of solving the simultaneous equations described above using molar extinction coefficients $\varepsilon_{A, 280}=206,999$ (estimated value), $\varepsilon_{A, 495}=0$, $\varepsilon_{D, 280}=8067$ (measured value) and $\varepsilon_{D, 495}=8121$ (measured value), the average drug binding number per antibody was 8.4.

Example 11

Figure 3:
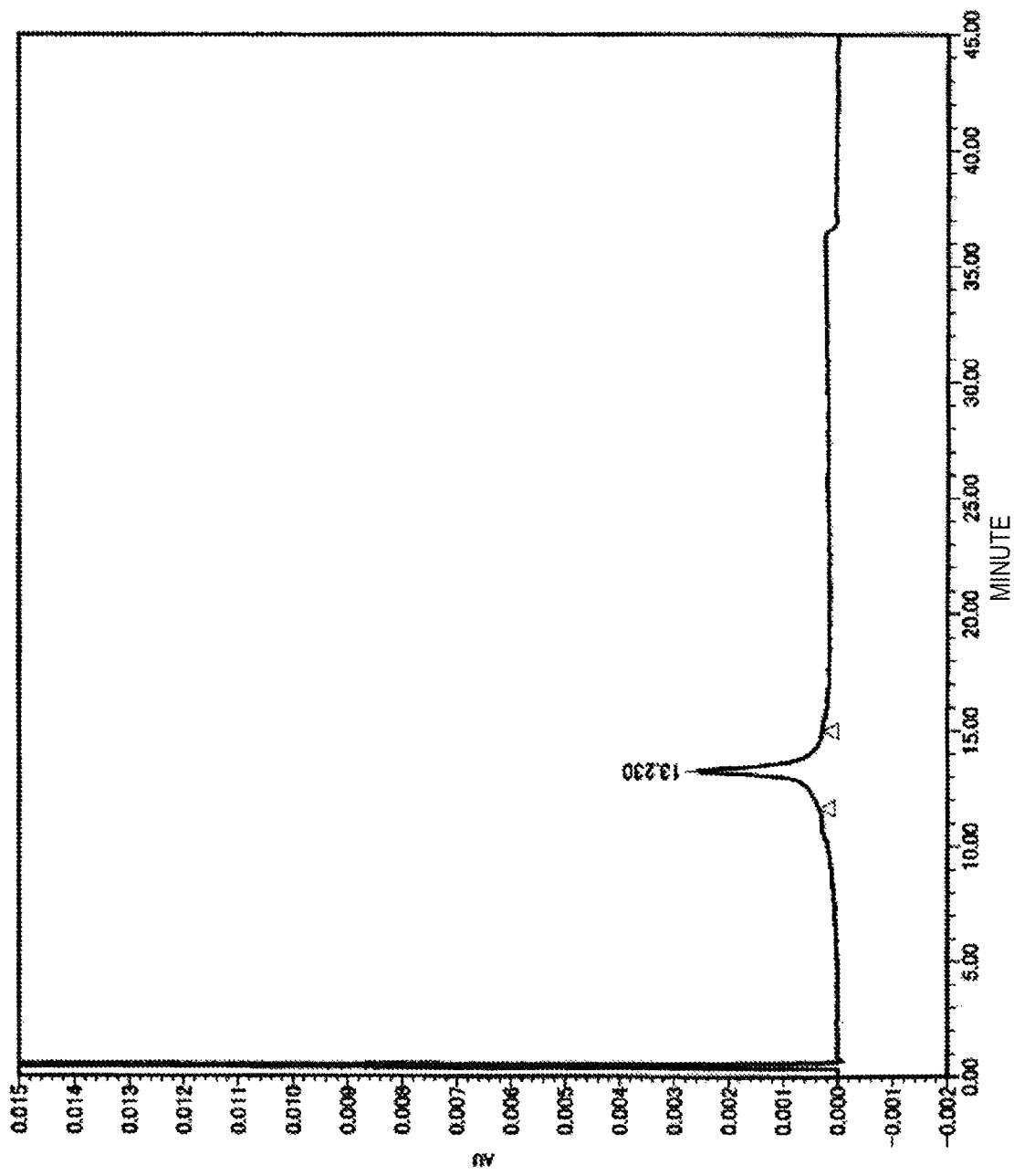
FIG. 3 is a chart of HPLC measurement using a hydrophobic interaction chromatography (HIC) column of Example 11 as to a drug-linker compound of formula (30) obtained in Example 7.

As to the drug-linker compound of formula (30) obtained in Example 7, HPLC measurement was performed using a hydrophobic interaction chromatography (HIC) column under the measurement conditions described below. A chart of the results at a measurement wavelength of 495 urn was shown in FIG. 3.

HPLC apparatus: Alliance (Waters)
Column: TSKgel Butyl-NPR (4.6×35 mm, 2.5 μm; Tosoh Corp.)
Flow rate: 0.8 mL/minute,
Analysis time: 45 minutes,
Column temperature: 25° C.,
Injection amount: 100 μL,
Detector: ultraviolet visible spectrophotometer (measurement wavelength: 495 nm and 280 nm)
Mobile phase A: 50 mM sodium phosphate buffer solution (pH 7.0) containing 1.5 M ammonium sulfate
Mobile phase B: A mixed solution containing 80% of 50 mM sodium phosphate buffer solution (PH 7.0) and 20% of isopropyl alcohol
Gradient program: 0% to 0% (0 minute to 2.5 minutes), 0% to 100% (2.5 minutes to 35 minutes), 100% to 0% (35.1 minutes to 45 minutes)

Example 12

Into a 300 mL four-necked flask equipped with a thermometer, a nitrogen inlet tube, a stirrer, a Dean-stark tube and a condenser tube were charged tetraethylene glycol monomethyl ether (23.0 g, 110 mmol), toluene (115 g), triethylamine (14.5 g, 143 mmol) and methanesulfonyl chloride (13.9 g, 121 mmol), and the reaction was performed at 40° C. for 2 hours. The reaction solution was diluted by adding dichloromethane and then washed with water, and the organic layer was dried over anhydrous magnesium sulfate. After filtration, the solvent was distilled off under a reduced pressure to obtain a compound of formula (31).

$^1$H-NMR (CDCl$_3$, internal standard TMS); δ (ppm):
3.08 (3H, s, —O—SO$_2$—C$\underline{H}_3$),
3.38 (3H, s, —O—C$\underline{H}_3$),
3.45-3.85 (14H, m, CH$_3$—O—(C$\underline{H}_2$C$\underline{H}_2$O)$_4$—C$\underline{H}_2$CH$_2$—O—SO$_2$—CH$_3$),
4.38 (2H, m, —C$\underline{H}_2$—O—SO$_2$—CH$_3$)

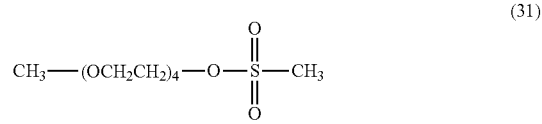

(31)

Example 13

Into a 500 mL four-necked flask equipped with a thermometer, a nitrogen inlet tube, a stirrer, a Dean-stark tube and a condenser tube were charged the compound of formula (24) (5.00 g, 24.1 mmol), dehydrated THF (138 g), compound of formula (31) (16.6 g, 57.9 mmol), 1M tert-butoxy potassium THF solution (52.6 g. 33.7 mmol), and the reaction was performed at 50° C. for 4 hours. After adding dichloromethane and an aqueous 25% by weight sodium chloride solution, water washing was performed, and the organic layer was dried over anhydrous sodium sulfate. After filtration, the solvent was distilled off under a reduced pressure to obtain a compound of formula (32).

$^1$H-NMR (CDCl$_3$, internal standard TMS); δ (ppm):
3.38 (6H, s, —O—C$\underline{H}_3$),
3.40-3.75 (36H, m, >C(CH$_2$O)$_2$—, —O—(C$\underline{H}_2$C$\underline{H}_2$O)$_4$—, —CNO—C$\underline{H}_2$—),
4.36 (2H, s, —CNO—C$\underline{H}_2$—),
7.37-7.94 (5H, m, arom.$\underline{H}$)

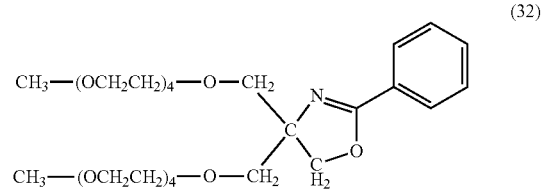

(32)

Example 14

To a 500 mL four-necked flask equipped with a thermometer, a nitrogen inlet tube, a stirrer, a Dean-stark tube and a condenser tube were added the compound of formula (32) (12.0 g, 20.4 mmol) and distilled water (168 g) to be dissolved. After adding 85% phosphoric acid (6.3 mL) to adjust pH to 1.5, the reaction was performed at 50° C. for 2 hours. After adding an aqueous 400 g/L sodium hydroxide solution (72.9 mL) with cooling, the reaction was performed at 50° C. for 5 hours. Subsequently, 6N hydrochloric acid was added to adjust pH to 2.0 added and then toluene and chloroform were added thereto to perform washing. Sodium chloride was added so as to provide an aqueous 25% sodium chloride solution and then, using an aqueous 400 g/L sodium hydroxide solution pH was adjusted to 12.5. Extraction was performed by using toluene, and the extract was dried over anhydrous sodium sulfate, filtered, and the solvent was distilled off under a reduced pressure to obtain a compound of formula (33).

¹H-NMR (CDCl₃, internal standard TMS); δ (ppm):
3.08 (1H, brs, —O$\underline{H}$),
3.38 (6H, s, —O—C$\underline{H}_3$),
3.40-3.80 (38H, m, >C(C$\underline{H}_2$O)₂—, —O—(C$\underline{H}_2$C$\underline{H}_2$O)₄—, >CNH₂—C$\underline{H}_2$—OH)

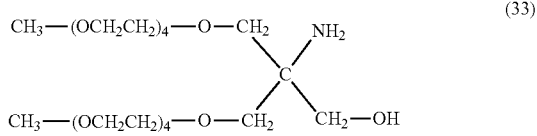

(33)

Example 15

Into a 100 mL three-necked flask equipped with a thermometer, a nitrogen inlet tube, a stirrer, a Dean-stark tube and a condenser tube were charged the compound of formula (33) (3.00 g, 5.98 mmol), 6-maleimidohexanoic acid (1.45 g, 6.88 mmol), DMT-MM (1.90 g, 6.88 mmol), acetonitrile (30.0 g) and triethylamine (0.726 g, 7.18 mmol), and the reaction was performed at 25° C. for 5 hours. Citrate buffer of pH 3.0 (36.0 g) was added thereto and then washing was performed by using toluene. Extraction was performed by using chloroform, and the organic layer was washed with an aqueous 10% sodium chloride solution. The organic layer was dried over anhydrous magnesium sulfate, filtered, and the solvent was distilled off under a reduced pressure to obtain a compound of formula (34).

¹H-NMR (CDCl₃, internal standard TMS); δ (ppm):
1.31 (2H, m, —C$\underline{H}_2$CH₂CH₂—CONH—),
1.62 (4H, m, —C$\underline{H}_2$CH₂C$\underline{H}_2$CH₂—CONH—),
2.18 (2H, t, —C$\underline{H}_2$—CONH—),
3.38 (6H, s, —O—C$\underline{H}_3$),
3.40-3.85 (40H, m, >C(C$\underline{H}_2$O)₂—, —O—(C$\underline{H}_2$C$\underline{H}_2$O)₄—, >CNH—C$\underline{H}_2$—OH, —C$\underline{H}_2$-maleimide),
4.62 (1H, t, —O$\underline{H}$),
6.23 (1H, s, —CH₂—CON$\underline{H}$—),
6.69 (2H, s, -maleimide)

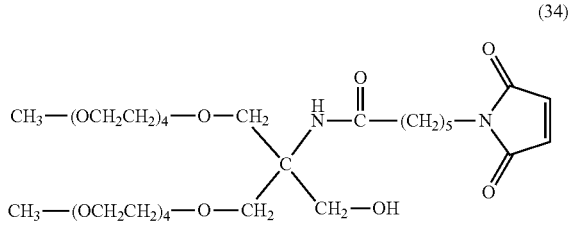

(34)

Example 16

To a 50 mL three-necked flask equipped with a thermometer, a nitrogen inlet tube, a stirrer, a Dean-stark tube and a condenser tube were added the compound of formula (34) (2.50 g, 3.60 mmol), N-phenylmorpholine (1.47 g, 9.00 mmol), p-nitrophenyl chloroformate (1.45 g, 7.20 mmol) and dichloromethane (47.7 g), and the reaction was performed at 25° C. for 2 hours. Distilled water (0.39 g, 21.6 mmol) and N-phenylmorpholine (1.47 g, 9.00 mmol) were added thereto, the mixture was stirred at 25° C. for 6 hours and then diluted by using hexane. The mixture was washed by using 0.2 M hydrochloric acid, borate buffer of pH 10 and then an aqueous 10% sodium chloride solution. The organic layer was dried over anhydrous sodium sulfate, filtered, and the solvent was distilled off under a reduced pressure. The residue was dissolved in acetonitrile. The solution was washed by adding hexane and tert-butanol, and the solvent was distilled off under a reduced pressure to obtain a compound of formula (35).

¹H-NMR (CDCl₃, internal standard TMS); δ (ppm):
1.31 (2H, m, —C$\underline{H}_2$CH₂CH₂—CONH—),
1.59 (4H, m, —C$\underline{H}_2$CH₂C$\underline{H}_2$CH₂—CONH—),
2.16 (2H, t, —C$\underline{H}_2$—CONH—),
3.38 (6H, s, —O—C$\underline{H}_3$),
3.40-3.85 (38H, m, >C(C$\underline{H}_2$O)₂—, —O—(C$\underline{H}_2$C$\underline{H}_2$O)₄—, —C$\underline{H}_2$-maleimide),
4.70 (1H, s, >CNH—C$\underline{H}_2$—OCOO—),
6.08 (1H, s, —CH₂—CON$\underline{H}$—),
6.69 (2H, s, -maleimide),
7.35-8.35 (4H, m, arom.$\underline{H}$)

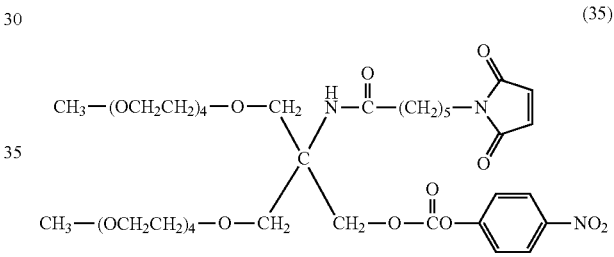

(35)

Comparative Example 1

Into a 100 mL three-necked flask equipped with a thermometer, a nitrogen inlet tube, a stirrer, a Dean-stark tube and a condenser tube were charged 2-amino-2-methyl-1,3-propanediol (13.1 g, 125 mmol), sodium carbonate (2.65 g, 25 mmol), dehydrated methanol (19.8 g) and benzonitrile (2.58 g, 25 mmol), and the reaction and purification were performed in the same manner as in Example 1 to obtain a compound of formula (36).

¹H-NMR (CD₃OD, internal standard TMS); δ (ppm):
1.33 (3H, s, >CC$\underline{H}_3$—CH₂—OH),
3.49-3.60 (2H, dd, >CCH₃—C$\underline{H}_2$—OH),
4.10-4.53 (2H, dd, —CNO—C$\underline{H}_2$—),
7.43-7.93 (5H, m, arom.$\underline{H}$)

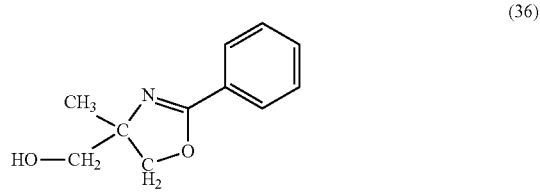

(36)

Comparative Example 2

Into a 50 mL three-necked flask equipped with a thermometer, a nitrogen inlet tube, a stirrer, a Dean-stark tube and a condenser tube were charged the compound of formula (36) (0.130 g, 0.680 mmol), dehydrated THF (1.87 g), the compound of formula (25) (0.651 g, 1.02 mmol), 1M tert-butoxy potassium THF solution (0.928 g. 1.02 mmol), and the reaction and purification were performed in the same manner as in Example 3 to obtain a compound of formula (37).

$^1$H-NMR (CDCl$_3$, internal standard TMS); δ (ppm):
1.37 (3H, s, >CC$\underline{H_3}$—CH$_2$—O—CH$_2$—),
3.38 (3H, s, —O—C$\underline{H_3}$),
3.40-3.80 (50H, m, >CCH$_3$—C$\underline{H_2}$—O—CH$_2$—, —O—(C$\underline{H_2}$CH$_2$O)$_2$—, —CNO—C$\underline{H_2}$—),
4.01-4.47 (2H, dd, —CNO—C$\underline{H_2}$—),
7.38-7.95 (5H, m, arom.$\underline{H}$)

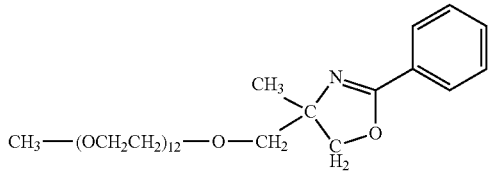
(37)

Comparative Example 3

To a 50 mL three-necked flask equipped with a thermometer, a nitrogen inlet tube, a stirrer, a Dean-stark tube and a condenser tube were added the compound of formula (37) (0.160 g, 0.218 mmol) and distilled water (4.40 g) to be dissolved. After adding 85% phosphoric acid (0.11 mL) to adjust pH to 1.5, the reaction was performed at 50° C. for 6 hours. After adding an aqueous 400 g/L sodium hydroxide solution (1.40 mL) with cooling, the reaction was performed at 50° C. for 5 hours. Subsequently, 6N hydrochloric acid was added to adjust pH to 2.0 and then toluene and chloroform were added thereto to perform washing. Thereafter, the purification was performed in the same manner as in Example 4 to obtain a compound of formula (38).

$^1$H-NMR (CDCl$_3$, internal standard TMS); δ (ppm):
1.03 (3H, s, >CC$\underline{H_3}$—CH$_2$—O—),
2.91 (1H, brs, —O$\underline{H}$),
3.38 (3H, s, —O—C$\underline{H_3}$),
3.00-3.85 (52H, m, >CCH$_3$—C$\underline{H_2}$—O—CH$_2$—, —O—(C$\underline{H_2}$CH$_2$O)$_{12}$—, >CCH$_3$—C$\underline{H_2}$—OH)

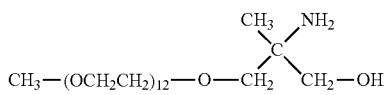
(38)

Comparative Example 4

Into a 4-mL screw tube containing a stirrer were charged the compound of formula (38) (0.0920 g, 0.142 mmol), 6-maleimidohexanoic acid (0.0345 g, 0.163 mmol), DMT-MM (0.0564 g, 0.163 mmol), acetonitrile (0.980 g) and triethylamine (0.0172 g, 0.170 mmol), and the reaction was performed at 25° C. for 5 hours. Citrate buffer of pH 3.0 (1.10 g) was added thereto and then washing was performed by using toluene. Thereafter, the purification was performed in the same manner as in Example 5 to obtain a compound of formula (39).

$^1$H-NMR (CDCl$_3$, internal standard TMS); δ (ppm):
1.27 (3H, s, >CC$\underline{H_3}$—CH$_2$—O—), 1.32 (2H, m, —C$\underline{H_2}$CH$_2$CH$_2$—CONH—),
1.63 (4H, m, —C$\underline{H_2}$CH$_2$C$\underline{H_2}$CH$_2$—CONH—), 2.18 (2H, t, —C$\underline{H_2}$—CONH—),
3.38 (3H, s, —O—C$\underline{H_3}$),
3.40-3.80 (54H, m, >CCH$_3$—C$\underline{H_2}$—O—CH$_2$—, —O—(C$\underline{H_2}$CH$_2$O)$_{12}$—, >CCH$_3$—C$\underline{H_2}$—OH, —C$\underline{H_2}$-maleimide),
4.62 (1H, brs, —O$\underline{H}$), 6.20 (1H, s, —CH$_2$—CON$\underline{H}$—),
6.69 (2H, s, -maleimide)

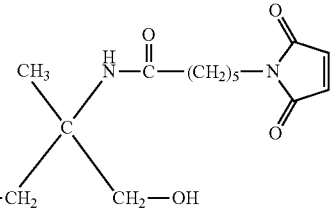
(39)

Comparative Example 5

To a 4-mL screw tube containing a stirrer were added the compound of formula (39) (0.050 g, 0.0595 mmol), N-methylmorpholine (0.0601 g, 0.595 mmol), Bis(4-nitrophenyl) carbonate (0.145 g, 0.476 mmol) and dehydrated acetonitrile (0.467 g), and the reaction was performed at 25° C. for 4 hours in a nitrogen atmosphere. Distilled water (0.030 g, 1.67 mmol) and N-methylmorpholine (0.0361 g, 0.357 mmol) were added thereto, the mixture was stirred at 25° C. for 6 hours and then diluted by using dichloromethane. Thereafter, the purification was performed in the same manner as in Example 5 to obtain a compound of formula (40).

$^1$H-NMR (CDCl$_3$, internal standard TMS); δ (ppm):
1.32 (2H, m, —C$\underline{H_2}$CH$_2$CH$_2$—CONH—), 1.45 (3H, s, >CC$\underline{H_3}$—CH$_2$—O—),
1.60 (4H, m, —C$\underline{H_2}$CH$_2$C$\underline{H_2}$CH$_2$—CONH—), 2.15 (2H, t, —C$\underline{H_2}$—CONH—),
3.38 (6H, s, —O—C$\underline{H_3}$),
3.41-3.80 (52H, m, >CCH$_3$—C$\underline{H_2}$—O—CH$_2$—, —O—(C$\underline{H_2}$CH$_2$O)$_{12}$—, —C$\underline{H_2}$-maleimide),
4.51-4.59 (2H, dd, >CCH$_3$—C$\underline{H_2}$—OCOO—),
5.92 (1H, s, —CH$_2$—CON$\underline{H}$—), 6.68 (2H, s, -maleimide),
7.39-8.29 (4H, m, arom.$\underline{H}$)

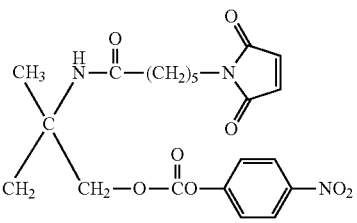
(40)

Comparative Example 6

Into a 4-mL screw tube containing a stirrer were charged doxorubicin hydrochloride (6.34 mg, 10.9 μmol), N,N-diisopropylamine (2.95 mg, 22.9 μmol), N,N-dimethylformamide and the compound of formula (40) (10.0 mg, 9.94 μmol), and the reaction was performed for 4 hours. After dilution with dichloromethane, the mixture was washed by using an aqueous 5% by weight sodium dihydrogen phosphate 12-hydrate solution and then using ion exchange water. The organic layer was dried over anhydrous sodium sulfate, filtered, and the solvent was distilled off under a reduced pressure to obtain a drug-linker compound of formula (41).

$^1$H-NMR (CD$_3$Cl, internal standard TMS); δ (ppm):
1.25-1.34 (8H, m), 1.55-1.65 (4H, m), 1.75-1.88 (2H, m),
2.06-2.10 (2H, m), 2.16-2.38 (2H, m), 2.88 (1H, dd),
3.00 (1H, s), 3.18 (2H, dd), 3.38 (3H, s),
3.41-3.90 (60H, m), 4.03-4.06 (1H, m), 4.09 (3H, s),
4.12-4.14 (1H, m), 4.61 (1H, s), 4.77 (2H, d),
5.32 (1H, s), 5.43-5.48 (1H, m), 5.53 (1H, s),
6.06 (1H, d), 6.68 (2H, s), 7.41 (1H, d),
7.80 (1H, t), 8.06 (1H, d)

Comparative Example 7

Figure 2:
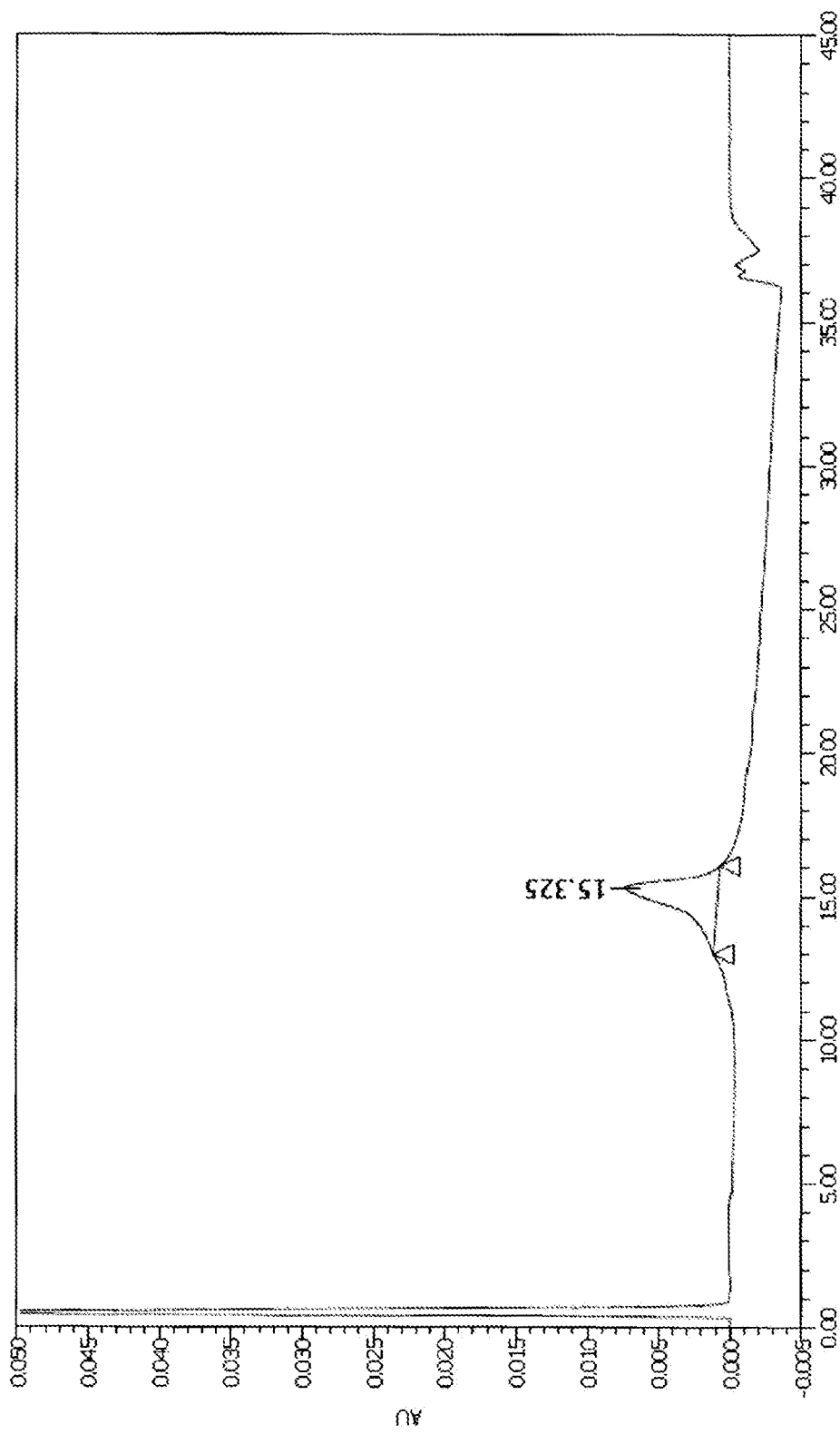
FIG. 2 is a chart of HPLC measurement using a hydrophobic interaction chromatography (HIC) column of Comparative Example 7.

As to the drug-linker compound of formula (41) obtained in Comparative Example 6, HPLC measurement was performed using a hydrophobic interaction chromatography (HIC) column under the same measurement conditions as in Example 8. A chart of the measurement results was shown in FIG. 2.

Comparative Example 8

Monoclonal anti-interleukin-1 beta antibody produced in mouse (0.500 mg, Sigma-Aldrich) was dissolved in phosphate buffered saline (PBS, 0.500 mL). The solution (0.048 mL) was put into a 0.5 mL polyethylene tube, 50.0 mM of ethylenediamine tetraacetic acid (EDTA, 0.006 mL) and an aqueous 0.800 mM tris(2-carboxymethyl)phosphine hydrochloride (TCEP) solution (0.006 mL; 15 equivalents to the antibody) were added thereto, and the mixture was shaken at 37° C. for one hour. To the solution was added a solution containing N,N-dimethylacetamide and 2.50 mM of the compound of formula (41) (0.007 mL; 53 equivalents to the antibody), and the mixture was further shaken at 20° C. for one hour. An aqueous 2.50 mM N-acetyl cysteine (0.007 mL; 53 equivalents to an antibody) solution was added thereto, and the resulting mixture was further shaken at 20° C. for one hour. The resulting solution was filled in a NAP-5 column (GE Healthcare Life Science) equilibrated by using PBS (10 mL) and eluted with PBS to separate an antibody fraction.

Comparative Example 9

The average drug binding number was calculated by the same method as in Example 10 and the average drug binding number per antibody was 8.5.

Comparative Example 10

Into a 50 mL three-necked flask equipped with a thermometer, a nitrogen inlet tube, a stirrer, a Dean-stark tube and a condenser tube were charged tetracosaethylene glycol monomethyl ether (2.05 g, 1.88 mmol), toluene (10.3 g), triethylamine (0.552 g, 5.45 mmol) and methanesulfonyl chloride (0.478 g, 4.17 mmol), and the reaction was performed at 25° C. for 8 hours. The reaction solution was diluted by adding dichloromethane and then washed with water, and the organic layer was dried over anhydrous magnesium sulfate. After filtration, the solvent was distilled off under a reduced pressure to obtain a compound of formula (42).

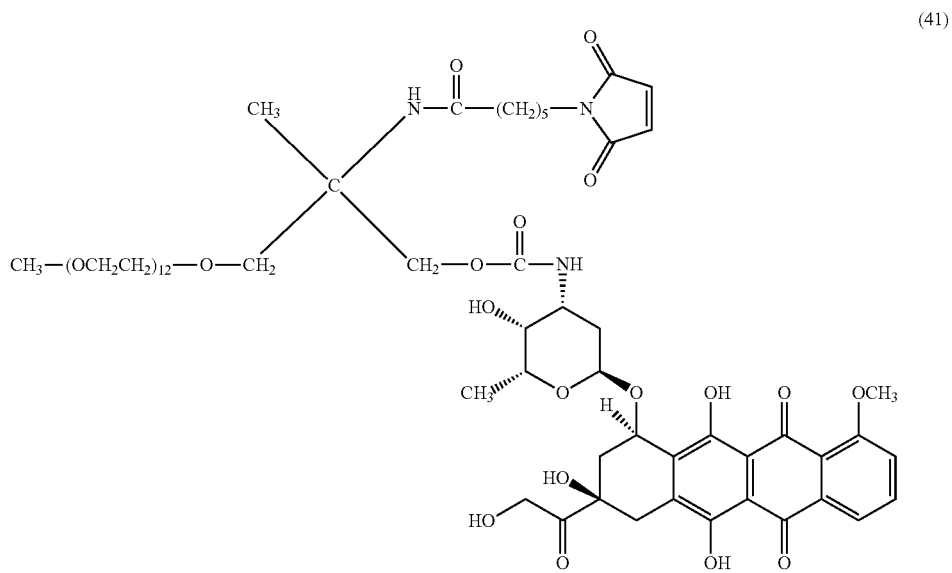

(41)

$^1$H-NMR (CDCl$_3$, internal standard TMS); δ (ppm):
3.09 (3H, s, —O—SO$_2$—C$\underline{H}_3$),
3.38 (3H, s, —O—C$\underline{H}_3$),
3.45-3.85 (94H, m, CH$_3$—O—(C$\underline{H}_2$C$\underline{H}_2$O)$_{23}$—C$\underline{H}_2$CH$_2$—O—SO$_2$—CH$_3$),
4.38 (2H, m, —C$\underline{H}_2$—O—SO$_2$—CH$_3$)

(42)

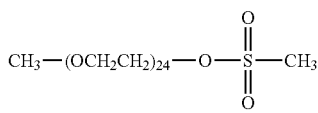

Comparative Example 11

Into a 50 mL three-necked flask equipped with a thermometer, a nitrogen inlet tube, a stirrer, a Dean-stark tube and a condenser tube were charged the compound of formula (36) (0.174 g, 0.910 mmol), dehydrated THF (2.86 g), the compound of formula (42) (1.38 g, 1.18 mmol), 1M tert-butoxy potassium THF solution (1.82 g. 2.00 mmol), and the reaction and purification were performed in the same manner as in Example 3 to obtain a compound of formula (43).

$^1$H-NMR (CDCl$_3$, internal standard TMS); δ (ppm):
1.37 (3H, s, >CC$\underline{H_3}$—CH$_2$—O—CH$_2$—),
3.38 (3H, s, —O—C$\underline{H_3}$),
3.40-3.80 (98H, m, >CCH$_3$—C$\underline{H_2}$—O—CH$_2$—, —O—(C$\underline{H_2}$C$\underline{H_2}$O)$_{24}$—),
4.01-4.47 (2H, dd, —CNO—C$\underline{H_2}$—),
7.38-7.95 (5H, m, arom.$\underline{H}$)

(43)

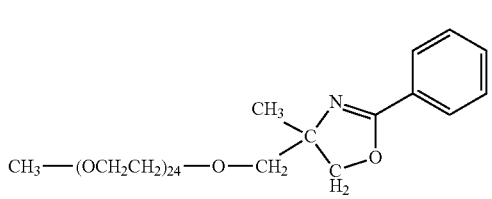

Comparative Example 12

To a 50 mL three-necked flask equipped with a thermometer, a nitrogen inlet tube, a stirrer, a Dean-stark tube and a condenser tube were added the compound of formula (43) (0.909 g, 0.720 mmol) and distilled water (25.0 g) to be dissolved. After adding 85% phosphoric acid (0.250 mL) to adjust pH to 1.5, the reaction was performed at 50° C. for 6 hours. After adding an aqueous 400 g/L sodium hydroxide solution (7.63 mL) with cooling, the reaction was performed at 50° C. for 10 hours. Subsequently, 6N hydrochloric acid was added to adjust pH to 2.0 and then toluene and chloroform were added thereto to perform washing. Thereafter, the purification was performed in the same manner as in Example 4 to obtain a compound of formula (44).

$^1$H-NMR (CDCl$_3$, internal standard TMS); δ (ppm):
1.03 (3H, s, >CC$\underline{H_3}$—CH$_2$—O—),
3.00 (1H, brs, —O$\underline{H}$),
3.38 (3H, s, —O—C$\underline{H_3}$),
3.00-3.85 (100H, m, >CCH$_3$—C$\underline{H_2}$—O—CH$_2$—, —O—(C$\underline{H_2}$C$\underline{H_2}$O)$_{24}$—, >CCH$_3$—C$\underline{H_2}$—O$\underline{H}$)

(44)

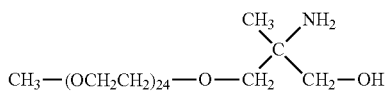

Comparative Example 13

Into a 50 mL three-necked flask equipped with a thermometer, a nitrogen inlet tube, a stirrer, a Dean-stark tube and a condenser tube were charged the compound of formula (44) (0.729 g, 0.620 mmol), 6-maleimidohexanoic acid (0.164 g, 0.775 mmol), DMT-MM (0.214 g, 0.775 mmol), acetonitrile (7.29 g) and triethylamine (0.082 g, 0.806 mmol), and the reaction was performed at 25° C. for 3 hours. Citrate buffer of pH 3.0 (8.75 g) was added thereto and then washing was performed by using toluene. Thereafter, the purification was performed in the same manner as in Example 5 to obtain a compound of formula (45).

$^1$H-NMR (CDCl$_3$, internal standard TMS); δ (ppm):
1.23 (3H, s, >CC$\underline{H_3}$—CH$_2$—O—),
1.32 (2H, m, —C$\underline{H_2}$CH$_2$CH$_2$—CONH—),
1.63 (4H, m, —C$\underline{H_2}$CH$_2$C$\underline{H_2}$CH$_2$—CONH—),
2.18 (2H, t, —C$\underline{H_2}$—CONH—),
3.38 (3H, s, —O—C$\underline{H_3}$),
3.40-3.80 (102H, m, >CCH$_3$—C$\underline{H_2}$—O—CH$_2$—, —O—(C$\underline{H_2}$CH$_2$O)$_{24}$—, >CCH$_3$—C$\underline{H_2}$—OH, —C$\underline{H_2}$-maleimide),
4.71 (1H, brs, —O$\underline{H}$),
6.26 (1H, s, —CH$_2$—CON$\underline{H}$—),
6.69 (2H, s, -maleimide)

(45)

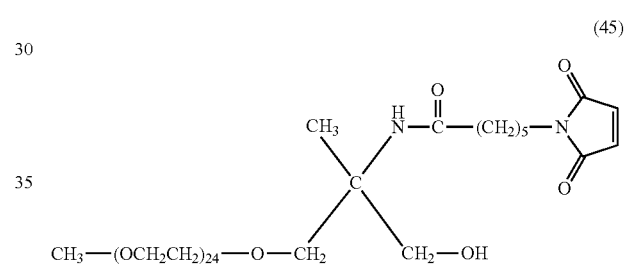

Comparative Example 14

To a 50 mL three-necked flask equipped with a thermometer, a nitrogen inlet tube, a stirrer, a Dean-stark tube and a condenser tube were added the compound of formula (45) (0.600 g, 0.438 mmol), N-phenylmorpholine (0.179 g, 1.10 mmol), p-nitrophenyl chloroformate (0.177 g, 0.876 mmol) and dichloromethane (5.81 g), and the reaction was performed at 25° C. for 3 hours. Distilled water (0.047 g, 2.63 mmol) and N-phenylmorpholine (0.179 g, 1.10 mmol) were added thereto, the mixture was stirred at 25° C. for 6 hours and then diluted by using hexane. Thereafter, the purification was performed in the same manner as in Example 16 to obtain a compound of formula (46).

$^1$H-NMR (CDCl$_3$, internal standard TMS); δ (ppm):
1.28 (2H, m, —C$\underline{H_2}$CH$_2$CH$_2$—CONH—),
1.41 (3H, s, >CC$\underline{H_3}$—CH$_2$—O—),
1.63 (4H, m, —C$\underline{H_2}$CH$_2$C$\underline{H_2}$CH$_2$—CONH—),
2.15 (2H, t, —C$\underline{H_2}$—CON$\underline{H}$—),
3.38 (3H, s, —O—C$\underline{H_3}$),
3.41-3.80 (100H, m, >CCH$_3$—C$\underline{H_2}$—O—CH$_2$—, —O—(C$\underline{H_2}$C$\underline{H_2}$O)$_{24}$—, —CH$_2$-maleimide),
4.51-4.60 (2H, dd, >CCH$_3$—C$\underline{H_2}$—OCOO—),
6.01 (1H, s, —CH$_2$—CON$\underline{H}$—),
6.69 (2H, s, -maleimide),
7.38-8.36 (4H, m, arom.$\underline{H}$)

(46)

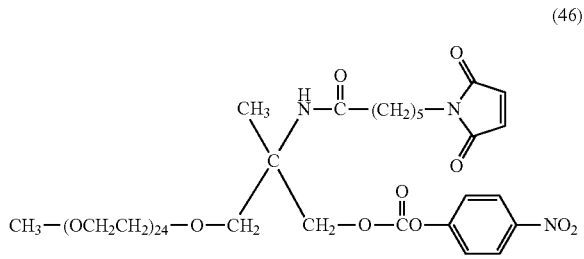

Comparative Example 15

Into a 4-mL screw tube containing a stirrer were charged doxorubicin hydrochloride (5.40 mg, 9.31 μmol), N,N-diisopropylamine (2.51 mg, 19.4 μmol), N,N-dimethylformamide and the compound of formula (35) (13.0 mg, 8.47 μmol), and the reaction was performed for 4 hours. Thereafter, the purification was performed in the same manner as in Example 7 to obtain a drug-linker compound of formula (47).

$^1$H-NMR (CDCl$_3$, internal standard TMS); δ (ppm):
1.25-1.34 (8H, m), 1.55-1.65 (4H, m), 1.75-1.88 (2H, m), 2.06-2.10 (2H, m), 2.16-2.38 (2H, m), 2.88 (1H, dd), 3.00 (1H, s), 3.18 (2H, dd), 3.38 (3H, s), 3.41-3.90 (103H, m), 4.03-4.06 (1H, m), 4.09 (3H, s), 4.12-4.14 (1H, m), 4.61 (1H, s), 4.77 (2H, d), 5.32 (1H, s), 5.43-5.48 (1H, m), 5.53 (1H, s), 6.06 (1H, d), 6.68 (2H, s), 7.41 (1H, d), 7.80 (1H, t), 8.06 (1H, d)

Comparative Example 16

As to the drug-linker compound of formula (41) obtained in Comparative Example 6, HPLC measurement was performed using a hydrophobic interaction chromatography (HIC) column under the same measurement conditions as in Example 11. A chart of the results at a measurement wavelength of 495 nm was shown in FIG. 4.

Comparative Example 17

As to the drug-linker compound of formula (47) obtained in Comparative Example 15, HPLC measurement was performed using a hydrophobic interaction chromatography (HIC) column under the same measurement conditions as in Example 11. A chart of the results at a measurement wavelength of 495 nm was shown in FIG. 5.

The drug-linker compound of formula (30) was detected at a retention time of 14.2 minutes of the chart of FIG. 1. On the other hand, the drug-linker compound of formula (41) was detected at a retention time of 15.3 minutes of the chart of FIG. 2. Therefore, it is shown that since the former drug-linker compound having a short retention time is less hydrophobic, the heterobifunctional monodispersed polyethylene glycol of the invention can effectively mask the hydrophobicity of the drug.

Figure 4:
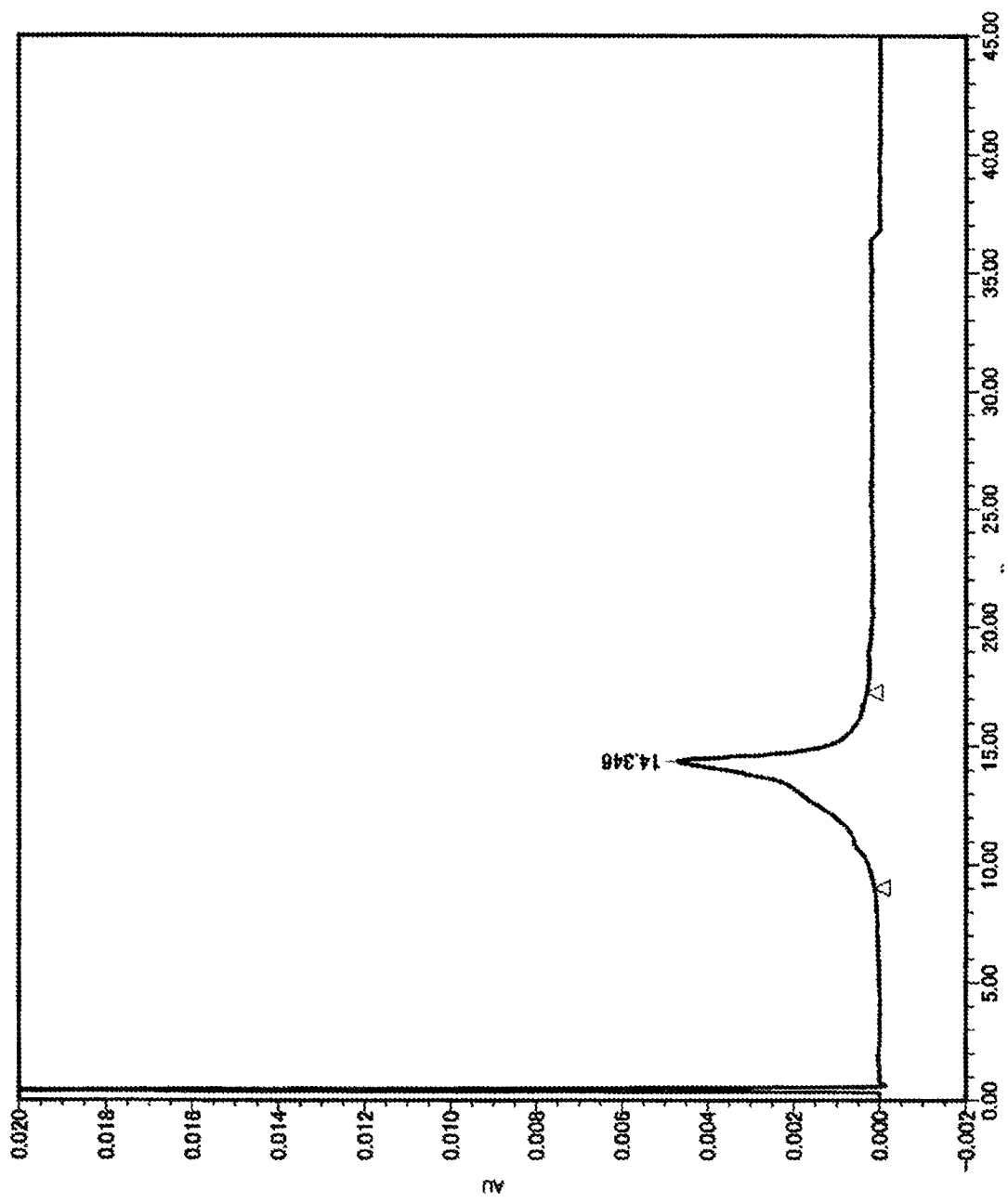
FIG. 4 is a chart of HPLC measurement using a hydrophobic interaction chromatography (HIC) column of Comparative Example 16 as to a drug-linker compound of formula (41) obtained in Comparative Example 6.
Figure 5:
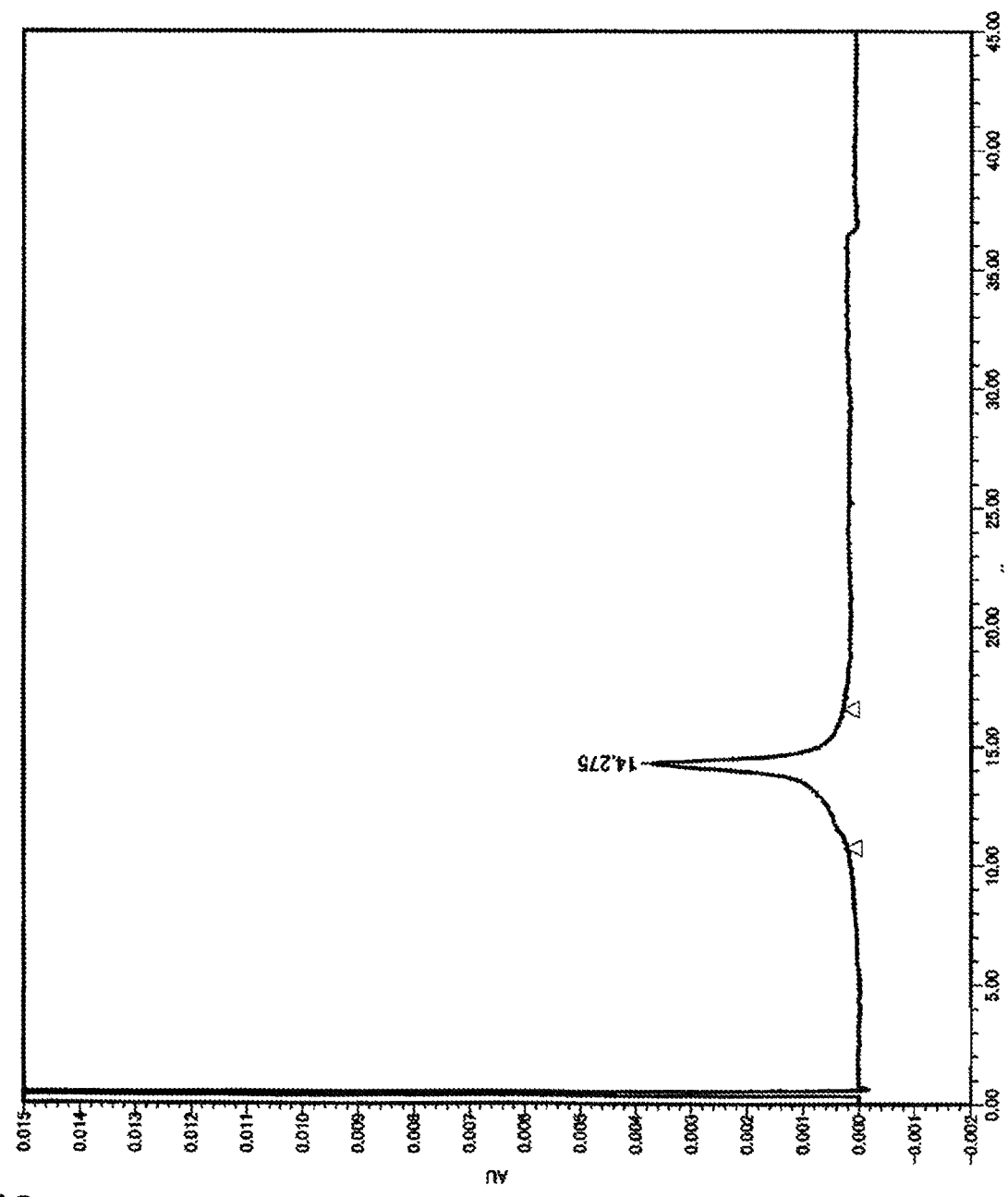
FIG. 5 is a chart of HPLC measurement using a hydrophobic interaction chromatography (HIC) column of Comparative Example 17 as to a drug-linker compound of formula (47) obtained in Comparative Example 15.

In the comparative examples, the drug-linker compound of formula (41) was detected at a retention time of 14.3 minutes of the chart of FIG. 4 and the drug-linker compound of formula (47) was detected at a retention time of 14.3 minutes of the chart of FIG. 5, and the retention time was on the same level regardless of the chain length of the monodispersed polyethylene glycol. On the other hand, the drug-linker compound of formula (30) according to the invention was detected at a retention time of 13.2 minutes of the chart of FIG. 3. Therefore, it is shown that since the drug-linker compound of formula (30) having a short retention time is less hydrophobic, the heterobifunctional monodispersed polyethylene glycol of the invention can effectively mask the hydrophobicity of the drug.

(47)

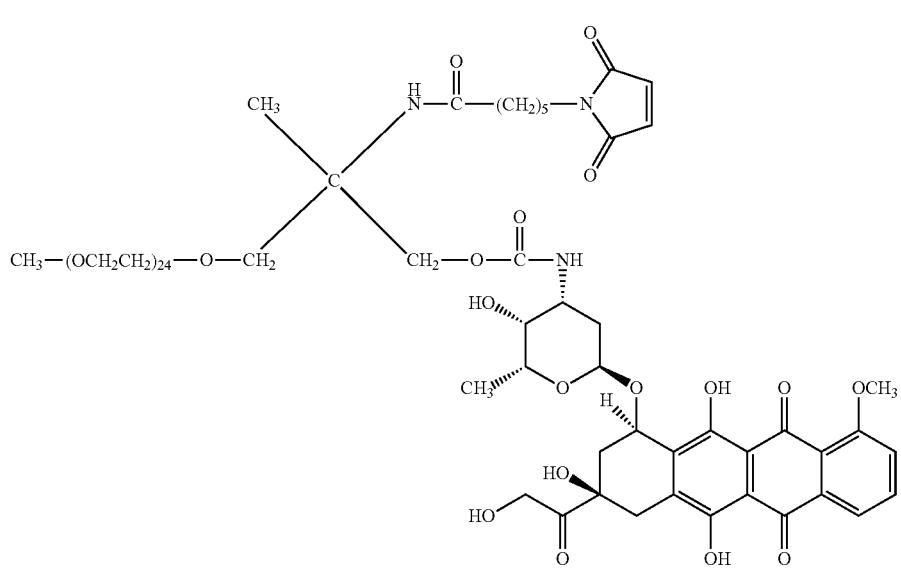

While the invention has been described in detail and with reference to specific embodiments thereof, it will be apparent to those skilled in the art that various changes and modifications can be made therein without departing from the spirit and scope of the invention.

This application is based on a Japanese patent application filed on Mar. 30, 2017 (Japanese Patent Application No. 2017-066987), and the whole contents thereof are incorporated herein by reference. Also, all the references cited herein are incorporated as a whole.

The invention claimed is:
1. A heterobifunctional monodispersed polyethylene glycol represented by formula (1):

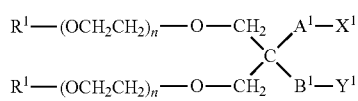

(1)

wherein, in the formula (1), $X^1$ and $Y^1$ are each an atomic group containing at least a functional group capable of forming a covalent bond upon a reaction with a functional group present in a biofunctional molecule, the functional group contained in the atomic group $X^1$ and the functional group contained in the atomic group $Y^1$ are different from each other; $R^1$ is a hydrocarbon group having from 1 to 7 carbon atoms; n is an integer of 3 to 72; $A^1$ represents —NHC(O)—$(CH_2)_{m1}$—, and m1 represents an integer of 1 to 5; and $B^1$ represents —$(CH_2)_{m3}$— or —$(CH_2)_{m3}$-$L^4$-$(CH_2)_{m4}$—, $L^4$ represents an ether bond, an amide bond or an urethane bond, and m3 and m4 represent each independently an integer of 1 to 5, wherein the functional group contained in the atomic group $X^1$ and the functional group contained in the atomic group $Y^1$ in the formula (1) are each independently selected from the group consisting of a vinyl sulfone group, formula (a), formula (b1), formula (b2), formula (c), formula (d), formula (e), formula (f), formula (g), formula (h), formula (i), formula (j), formula (k), formula (l), formula (m), formula (n) and formula (o):

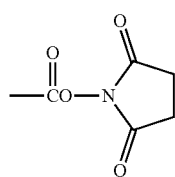

(a)

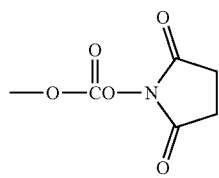

(b1)

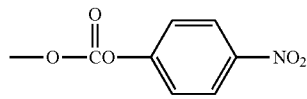

(b2)

(c)

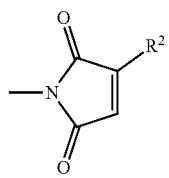

(d)

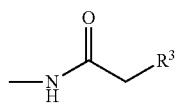

(e)

—COOH (f)

—SH (g)

(h)

—$NH_2$ (i)

—O—$NH_2$ (j)

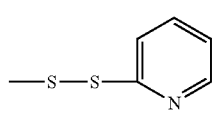

(k)

(l)

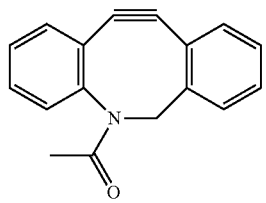

(m)

—$N_3$ (n)

—OH (o)

wherein, in the formula (d), $R^2$ is a hydrogen atom or a hydrocarbon group having from 1 to 5 carbon atoms; in the formula (e), $R^3$ is a halogen atom selected from a chlorine atom, a bromine atom and an iodine atom; and in the formula (1), $R^4$ is a hydrogen atom or a hydrocarbon group having from 1 to 5 carbon atoms.

2. The heterobifunctional monodispersed polyethylene glycol as claimed in claim 1, wherein the functional group contained in the atomic group $X^1$ and the functional group contained in the atomic group $Y^1$ in the formula (1) are each independently selected from the group consisting of a vinyl sulfone group, formula (a), formula (1), formula (b2), formula (c), formula (d), formula (e), formula (f), formula (g), formula (h), formula (i), formula (j), formula (k), formula (l), formula (n) and formula (o).

* * * * *